United States Patent
Shiau et al.

(10) Patent No.: US 10,793,527 B2
(45) Date of Patent: Oct. 6, 2020

(54) ADENOSINE MONOPHOSPHATE-ACTIVATED PROTEIN KINASE AGONIST

(71) Applicant: NATIONAL YANG-MING UNIVERSITY, Taipei (TW)

(72) Inventors: Chung-Wai Shiau, Taipei (TW); Jung-Chen Su, Taipei (TW); Yan-Ju Lin, Taipei (TW); Jui-Wen Huang, Taipei (CN)

(73) Assignee: NATIONAL YANG-MING UNIVERSITY, Taipei (TW)

( * ) Notice: Subject to any disclaimer, the term of this patent is extended or adjusted under 35 U.S.C. 154(b) by 0 days.

(21) Appl. No.: 16/331,388

(22) PCT Filed: Sep. 6, 2017

(86) PCT No.: PCT/CN2017/100735
§ 371 (c)(1),
(2) Date: Mar. 7, 2019

(87) PCT Pub. No.: WO2018/045969
PCT Pub. Date: Mar. 15, 2018

(65) Prior Publication Data
US 2019/0194142 A1 Jun. 27, 2019

Related U.S. Application Data

(60) Provisional application No. 62/384,195, filed on Sep. 7, 2016.

(51) Int. Cl.
| | | |
|---|---|---|
| *C07D 233/96* | (2006.01) |
| *A61P 35/00* | (2006.01) |
| *C07D 239/42* | (2006.01) |
| *C07D 401/14* | (2006.01) |
| *A61P 3/06* | (2006.01) |
| *C07D 403/04* | (2006.01) |
| *C07D 409/04* | (2006.01) |

(52) U.S. Cl.
CPC ............ *C07D 233/96* (2013.01); *A61P 3/06* (2018.01); *A61P 35/00* (2018.01); *C07D 239/42* (2013.01); *C07D 401/14* (2013.01); *C07D 403/04* (2013.01); *C07D 409/04* (2013.01)

(58) Field of Classification Search
CPC ...... C07D 233/96; C07D 239/42; A61P 35/00
See application file for complete search history.

(56) References Cited

U.S. PATENT DOCUMENTS

| | | | |
|---|---|---|---|
| 9,028,833 B2 * | 5/2015 | Govindan | A61K 47/6851 424/181.1 |
| 2012/0238540 A1 * | 9/2012 | Holcomb | C07D 239/42 514/210.18 |
| 2013/0209488 A1 * | 8/2013 | Sukhatme | A61K 31/196 424/158.1 |
| 2014/0031356 A1 * | 1/2014 | Azam | A61K 31/12 514/248 |

FOREIGN PATENT DOCUMENTS

| WO | WO 2011046970 A1 | 4/2011 |
|---|---|---|
| WO | WO 2011080277 A1 | 7/2011 |
| WO | WO 2013022278 A2 | 2/2013 |

* cited by examiner

*Primary Examiner* — D Margaret M Seaman
(74) *Attorney, Agent, or Firm* — Muncy, Geissler, Olds & Lowe, P.C.

(57) ABSTRACT

The present invention discloses a compound of the formula (I), which acts as an agonist of adenosine monophosphate-activated protein kinase, which induce phosphorylation and activation of AMPKα, thereby further regulating downstream signaling pathways, inhibiting growth and proliferation of liver cancer cells and breast cancer cells, and also inducing apoptosis of adipocytes. Therefore, the compound provided by the present invention can be utilised for treatment and preparation of pharmaceutical composition for cancer, and lipid metabolism-related diseases or syndromes mediated by AMPK.

Formula (I)

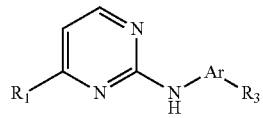

14 Claims, 7 Drawing Sheets

ADENOSINE MONOPHOSPHATE-ACTIVATED PROTEIN KINASE AGONIST

BACKGROUND OF THE INVENTION

Technical Field of the Invention

The present invention relates to a novel compound and its use, in particular to a compound, which is an adenosine monophosphate-activated protein kinase (AMPK) agonist and can be used for the treatment of AMPK-related cancer, lipid metabolic disorder or syndrome.

Background

Adenosine monophosphate-activated protein kinase (AMPK) is a complex of three subunits of α, β, and γ, which is an important regulator of metabolic reactions in eukaryotic cells. When the AMPK is activated by the regulation of upstream factors, it further regulates downstream signaling molecules, such as HIF-1, TSC1, TSC2, Raptor, UILK1, SREBP-1, SirT1, P300, HNF4α, Torc2, HDAC4, MBS85, MYPT1, Tau, CLIP170, ATGL, HSL, ACC, HMG-CoA, PFKFB3, GS, and TCB1D1.

The metabolic reactions regulated by AMPK directly relate to cell growth and survival. The inactivated or low activity form of AMPK is dominant in cancer, obesity, diabetes and aging-related diseases. AMPK is converted to activated form by phosphorylation, processing protein kinase activity to further phosphorylate downstream molecules to trigger or inhibit signaling pathways. In some studies, activated. AMPK inhibited the growth and survival of cancer cells and adipocytes, and the equivalent effect was observed in *Caenorhabditis elegans*. Thus, the activation of AMPK plays a key role in cells, making it a potential target for drug development and disease treatment.

AMPK agonist can be subdivided into indirect and direct activators. The direct AMPK activators have binding specificity for each subunit in the AMPK complex, that is, they affect the protein kinase activity through directly binding to AMPK, therefore, the clinical application of the direct AMPK activators is broader than that of the indirect AMPK activators. At present, several direct AMPK activators has entered the clinical trial phase, in which compound A-769662 and compound 911 are representative candidates. Most of the existing direct AMPK activators are specific for the regulatory subunit (AMPKβ2) or the ATP-sensing subunit (AMPKγ) in the AMPK complex, whereas few compounds target the active subunit (AMPKα). Therefore, this present invention aims to design and develop novel agonist specific for AMPKα.

SUMMARY OF INVENTION

Accordingly, the present invention provides a novel compound as shown in Formula (I):

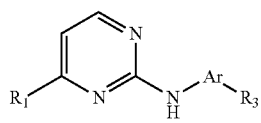

Formula (I)

wherein $R_1$ is an unsubstituted or substituted aromatic group; $R_3$ is a substituted phenyl amide group or a substituted phenyl urea group; Ar is an unsubstituted or substituted phenylene group.

In one embodiment, the unsubstituted or substituted phenylene group is

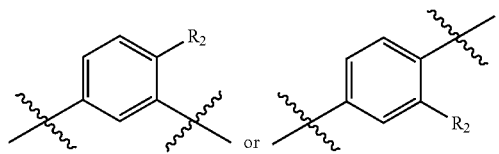

and $R_2$ is a hydrogen atom, a halide, or an alkyl group.

In one embodiment, $R_1$ is an unsubstituted aromatic group, a substituted aromatic group, a substituted

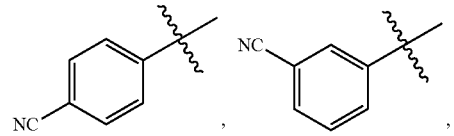

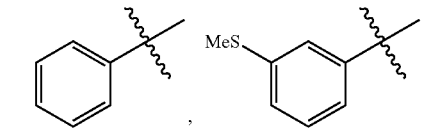

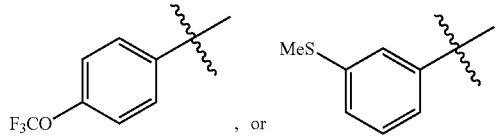

In one embodiment, $R_1$ is an unsubstituted pyrrolic group, a substituted pyrrolic group, or a substituted

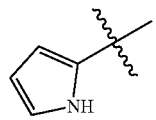

In one embodiment, $R_1$ is an unsubstituted thiophene group, a substituted thiophene group, or a substituted

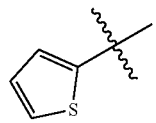

In one embodiment, $R_1$ is an unsubstituted naphthalenic group, a substituted naphthalenic group, or a substituted

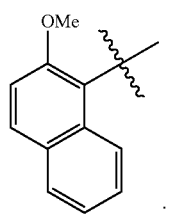 [SMILES: *c1c(OC)ccc2ccccc12]

In one embodiment, $R_1$ is a di-substituted phenyl group, a substituted

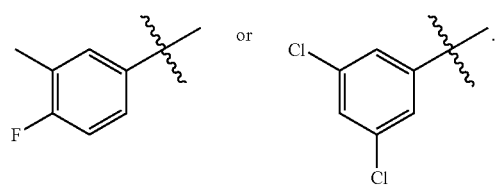

In one embodiment, the substituted phenyl amide group of $R_3$ is a substituted

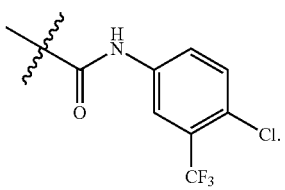

In one embodiment, the substituted phenyl urea group of $R_3$ is a substituted

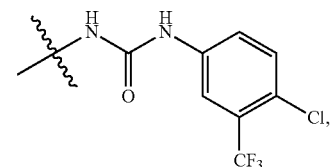

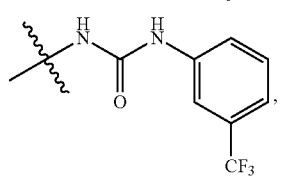

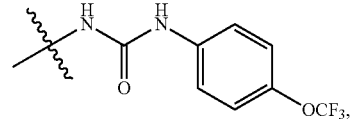

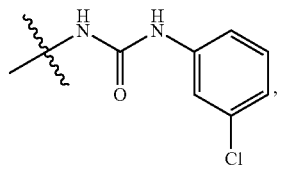

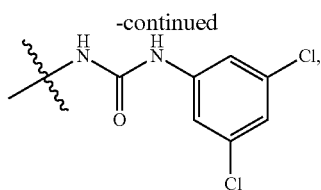

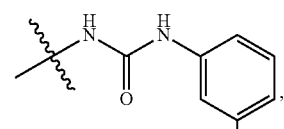

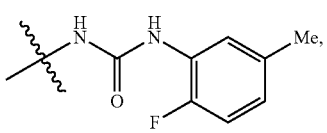

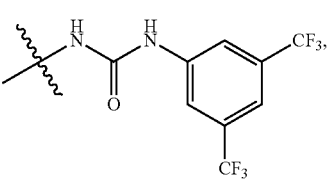

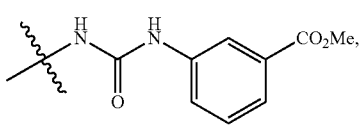

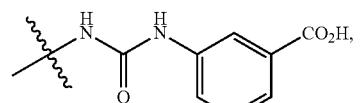

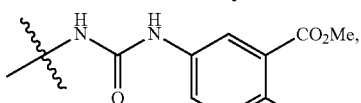

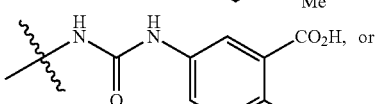

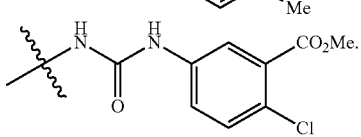

In one embodiment, the halide of $R_2$ is a fluoride or a chloride.

In one embodiment, the alkyl group of $R_2$ is a methyl group or an ethyl group.

In another aspect, the present invention is based on the above compounds, providing a use of the compounds for the preparation of a pharmaceutical composition, and the said pharmaceutical composition is used for AMPK-related cancer, lipid metabolic disorder or syndrome.

In another aspect, the present invention also provides for the use of an effective amount of the compound or a pharmaceutically acceptable salt thereof for the treatment of a disease, and the said disease is an AMPK-related cancer, lipid metabolic disorder or syndrome.

In one embodiment, the cancer is hepatic cancer or breast cancer.

In one embodiment, the compound activates AMPK through binding and phosphorylating a subunit of AMPK.

In one embodiment, the compound induces apoptosis of adipocytes.

DETAILED DESCRIPTION OF THE INVENTION

Definitions

Figure 1A:
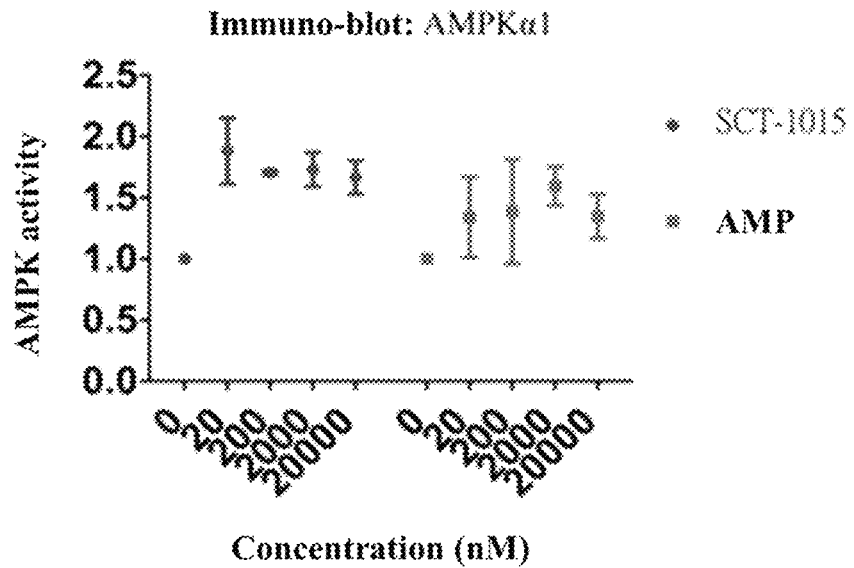
FIGS. 1A and 1B depict the compounds of the invention activate AMPK.

The term "aromatic group" refers to a cyclic planar molecule with resonant bonds that is more stable than other geometric or connected structures of the same atom groups. Since the most common aromatic compound is benzene, "aromatic" is also known as a benzene derivative.

The term "Ar" refers to an organic compound containing group of aromatic ring,

The term "phenyl amide group" refers to a group whose scaffold structure is a $C_6H_6N^-$.

The term "phenyl urea group" refers to a group whose scaffold structure is a C☐H☐NHCONH.

The term "phenylene group" refers to a group whose scaffold structure is a di-substituted benzene ring.

The term "halide" refers to fluoride, chloride, bromide, and iodide.

The term "alkyl group" refers to a chain-like organic functional group containing only atoms of carbon and hydrogen.

The term "substituted" refers to a plurality of substitutions are made by a named substituent; if a plurality of substituent moieties is disclosed or claimed, the substituted compound may independently be derived from one or more of the disclosed or claimed substituent moieties. The substitution is singly or plurally; in addition, independently substituted means that the (two or more) substituents may be the same or different.

The term "pharmaceutically acceptable" as used in this specification refers to a compound, material, composition, salt, and/or dosage form that are safe and suitable for administration to humans or animals, and in compliance with all applicable government regulations.

The term "effective amount" refers to an amount of the compound of the invention which means (1) treating or preventing a particular disease, symptom or disorder; (2) reducing, alleviating or eliminating one or more symptoms of a particular disease; or (3) prevent or delay the onset of one or more symptoms of a particular disease, symptom or disorder described herein.

The term "treatment" means reversing, alleviating, inhibiting the progression of a disease to which it is applied, delaying its onset or preventing the disease.

The pharmaceutical composition and treatment of the present invention may be administered in any suitable manner to provide a mammalian (especially human) effective amount of compound of the present invention. For example, oral, rectal, topical, parenteral, transocular, transpulmonary, and nasal may be employed.

The dosage form includes a tablet, a troches, a dispersing agent, a suspension, a solution, a capsule, a cream, an ointment, an aerosol, and the like, but not limited thereto. Preferably, the compound of the present invention is orally administered.

The subject of the present invention includes a mammalian individual. The said mammalian includes, but is not limited to, a cat, a cow, a goat, a horse, a sheep, a pig, a rodent, a rabbit, a primate, and the like, and includes an unborn mammalian. In a preferred embodiment, the human is a suitable individual, and the human individual can be of any gender and at any stage of development.

Efficacy

The compound disclosed in the present invention is an agonist of APMK, which binds to the APMKα subunit and activates AMPKα through phosphorylation, thereby regulating the downstream signaling pathway mediated by AMPKα, thereby inhibiting the growth of cancer cells and inducing the apoptosis of adipocytes. Therefore, the compounds of the present invention and pharmaceutically acceptable salts thereof are effective for treating diseases or conditions mediated by AMPK or otherwise associated with AMPK, such as cancer, metabolic disorder, lipodystrophy diseases, lipodystrophy syndrome, diabetes and aging-related diseases, but not limited to this.

The features and advantages of the present invention are further exemplified and illustrated in the following embodiments, which are merely illustrative and not intended to limit the scope of the invention.

Synthesis of the compounds of the invention.

The following schemes and examples are flowcharts for synthesizing the compounds of Formula I, which are merely illustrative of the technical spirit of the present invention, and not intended to limit the scope of the invention.

First general scheme of synthesis of the compound of the invention (Scheme I)

Scheme I

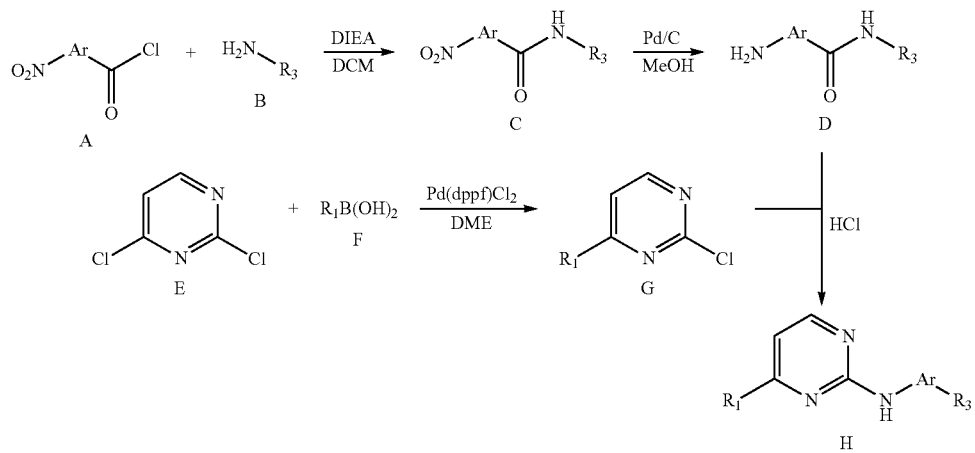

In the first step of the above Scheme the compound A and the compound B are subjected to a coupling reaction in the presence of N,N-diisopropylethylamine (DIEA) to produce an intermediate product C. DIEA is first added to Compound. B (dissolved in DMSO) at 4° C., and then Compound A is added to obtain a mixed solution, which is stirred at 4° C. for 5 minutes. The reaction is carried out at room temperature for 3 hours, and then ice water is added to quench the reaction. The reaction mixture is extracted with 100 ml of ethyl acetate to obtain an organic layer. The organic layer is washed with brine and then dehydrated with anhydrous magnesium sulfate ($MgSO_4$) and filtered. The filtered solution is concentrated and purified by column chromatography to obtain an intermediate Compound C. The intermediate Compound C is subjected to a hydration reaction in the presence of hydrogen and Palladium/charcoal. The mixture is filtered and purified by column chromatography to obtain compound D. On the other hand, compound E is coupled with substituted boronic acid F in the presence of (1,1'-Bis(diphenylphosphino)ferrocene)palladium(II) dichloride; $Pd(dppf)_2Cl_2$) to obtain compound G. In this reaction, Compound F (dissolved in DME, dehydrated) is mixed with boronic acid F and $Pd(dppf)_2Cl_2$ and heated to 90° C. in nitrogen. The solution is cooled to room temperature, filtered, concentrated and purified by chromatography column to obtain compound G. In the final step, the compound G and the compound D are coupled in isopropanol alcohol (IPA) by adding a catalytic amount of hydrochloric acid (HCl). The mixture was heated at 100° C. for 8 hours, extracted with 100 ml of ethyl acetate, and the obtained organic layer was washed with brine, dried over anhydrous magnesium sulfate ($MgSO_4$), and filtered. The filtered solution is then concentrated and purified by column chromatography to obtain compound H.

In the above Scheme I, $R_1$ is an unsubstituted or substituted aromatic ring group, for example, an unsubstituted or substituted phenyl group or a substituted

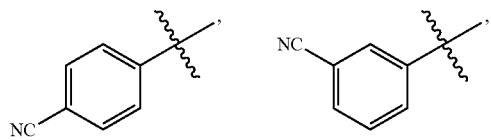

-continued

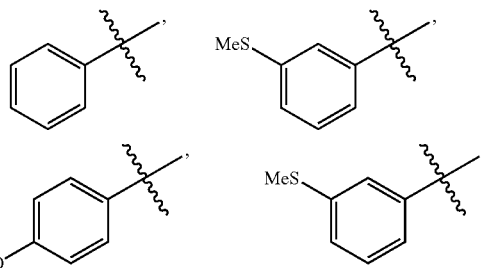

an unsubstituted pyrrolic group, a substituted pyrrolic group, a substituted

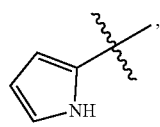

an unsubstituted thiophene group, a substituted thiophene group, a substituted

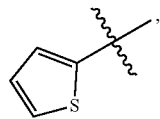 [SMILES: *c1cccs1]

an unsubstituted naphthalenic group, a substituted naphthalenic group, a substituted

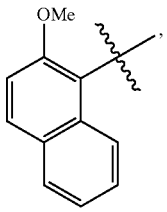 [SMILES: *c1c(OC)ccc2ccccc12]

a di-substituted phenyl group, a substituted

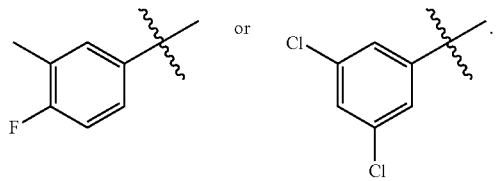

Further, in the above Scheme I, $R_3$ may be a substituted phenyl amide, such as a substituted

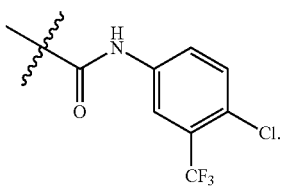

$R_3$ may be a substituted phenyl urea group, such as a substituted

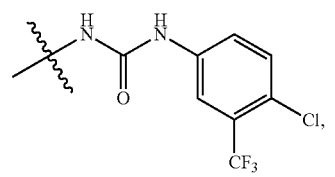

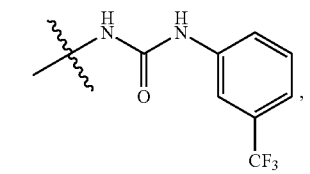

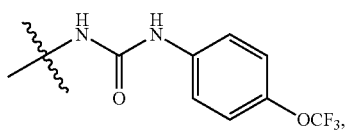

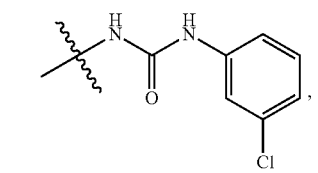

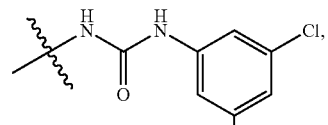

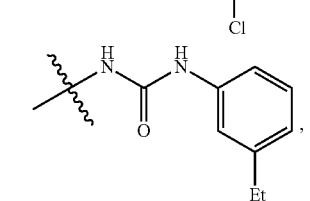

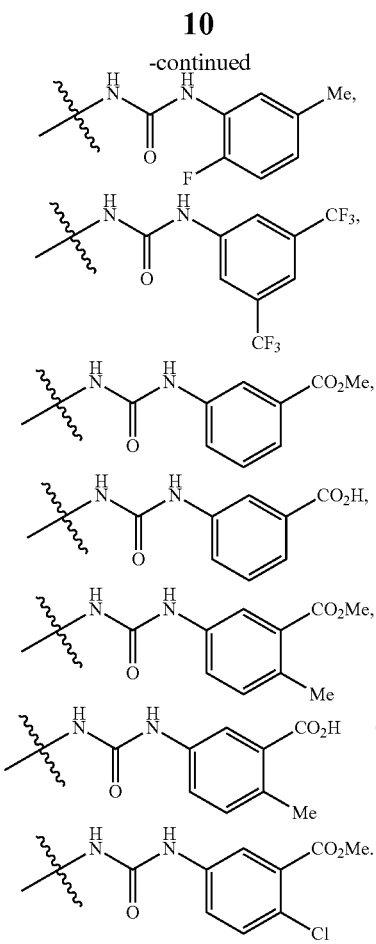

Further, in the above Scheme I, Ar may be an unsubstituted or substituted phenyl group, for example:

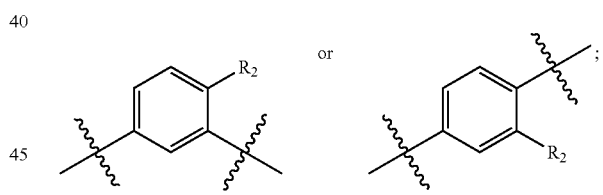

wherein, $R_2$ may be a hydrogen atom, a halide or an alkyl group. In some preferred embodiments, the halide is fluoride or chloride, and the alkyl group is methyl group or ethyl group.

The derivatives as listed in Table 1 can be synthesized by the above Scheme I.

TABLE 1 the derivatives of the present invention

| SCT | $R_1$ | $R_2$ | $R_3$ |
|---|---|---|---|
| 1001 | <img/> | Me | <img/> |

TABLE 1-continued the derivatives of the present invention

| SCT | R₁ | R₂ | R₃ |
|---|---|---|---|
| 1002 | 3-NC-phenyl | Me | -C(O)NH-(4-Cl-3-CF₃-phenyl) |
| 1003 | 1H-pyrrol-2-yl | Me | -C(O)NH-(4-Cl-3-CF₃-phenyl) |
| 1004 | phenyl | Me | -C(O)NH-(4-Cl-3-CF₃-phenyl) |
| 1005 | 2-OMe-naphthalen-1-yl | Me | -C(O)NH-(4-Cl-3-CF₃-phenyl) |
| 1007 | thiophen-2-yl | Me | -C(O)NH-(4-Cl-3-CF₃-phenyl) |
| 1008 | 3-MeS-phenyl | Me | -C(O)NH-(4-Cl-3-CF₃-phenyl) |
| 1009 | 4-F-3-Me-phenyl | Me | -C(O)NH-(4-Cl-3-CF₃-phenyl) |
| 1010 | 4-F₃CO-phenyl | Me | -C(O)NH-(4-Cl-3-CF₃-phenyl) |
| 1011 | 4-F₃C-phenyl | Me | -C(O)NH-(4-Cl-3-CF₃-phenyl) |
| 1012 | 3,5-diCl-phenyl | Me | -C(O)NH-(4-Cl-3-CF₃-phenyl) |

Embodiment 1 Synthesis of Compound SCT-1001

SCT-1001 is synthesized by the following Scheme II:

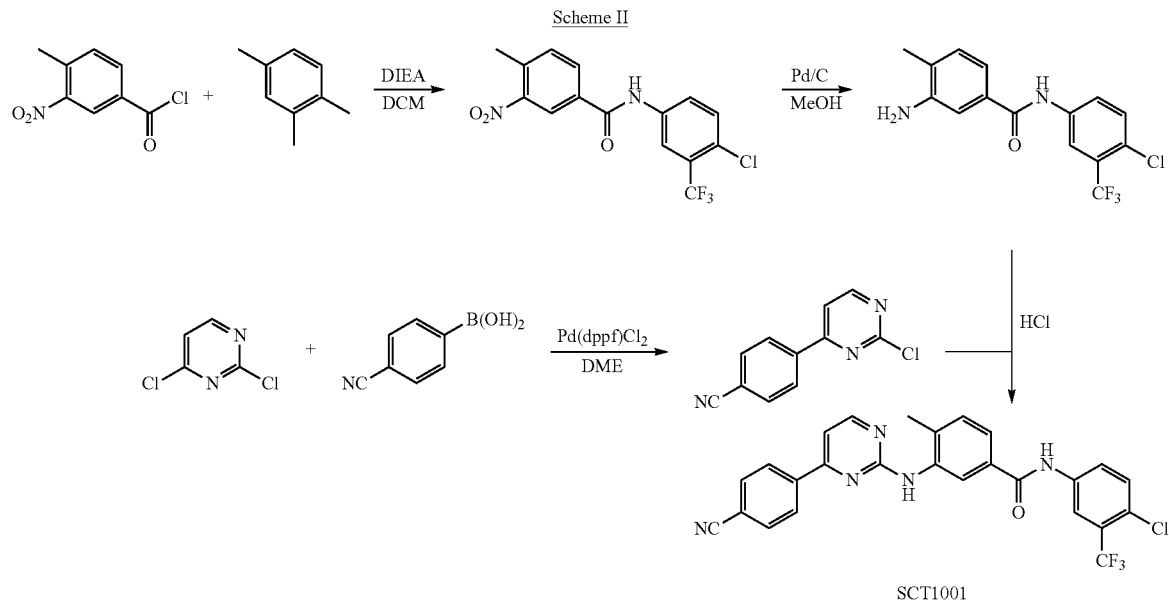

SCT1001

4-methyl-3-nitrobenzoyl chloride is first coupled to 5-chloro-3-(trifluoromethyl)aniline, followed by reduction of the intermediate under the catalysis of Pd/C to reduce the nitrogen group to the amine group. On the other hand, 2,4-dichloropyrimidine is coupled with 4-cyanophenylboronic acid to obtain 4-(2-chloropyrimidin-4-yl)benzonitrile.

concentrated and purified by column chromatography to obtain N-(4-chloro-3-(trifluoromethyl)phenyl)-3-((4-(4-cyanophenyl)pyrimidin-2-yl)amino)-4-methylbenzamide, which is the compound SCT-1001.

Second General Scheme of Synthesis of the Compound of the Invention (Scheme I)

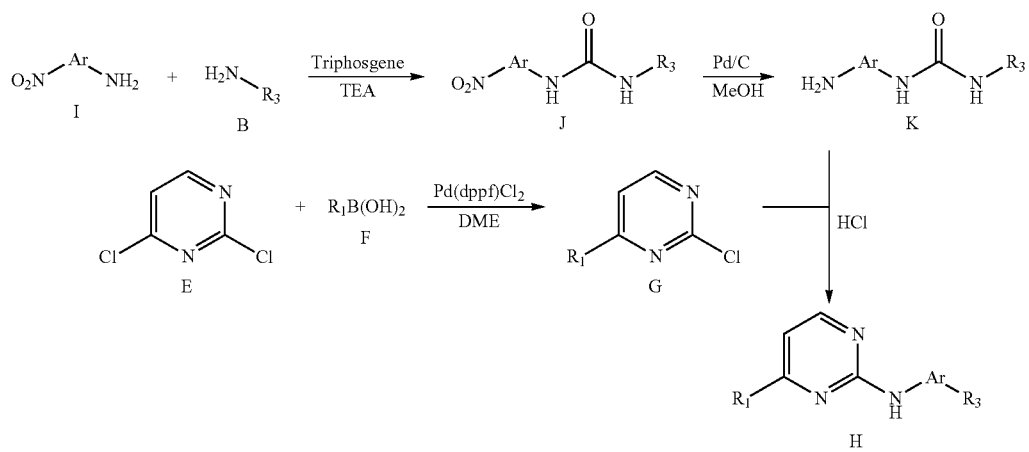

Next, 4-(2-chloropyrimidin-4-yl)benzonitrile is coupled to the aforementioned amine group to obtain the compound SCT1001.

In the first step of Scheme II, the intermediate 4-(2-chloropyrimidin-4-yl)benzonitrile is synthesized. 2,4-dichloropyrimidine (dissolved in DME), 4-cyanophenyl boronic acid and 1,1'-Bis(diphenylphosphino)ferrocene)palladium(II) dichloride, Pd(dppf)Cl$_2$ are mixed with 3 equivalents of triethylamine. The mixture is heated at 90° C. for 3 hours, filtered, concentrated and purified to obtain the intermediate 4-(2-chloropyrimidin-4-yl)benzonitrile.

4-(2-chloropyrimidin-4-yl)benzonitrile $^1$H NMR (400 MHz, CDCl3): δ 8.73 (d, J=5.2 Hz, 1H), 8.20 (d, J=8.4 Hz, 2H), 7.81 (d, J=8.4 Hz, 2H), 7.62 (d, J=5.2 Hz, 1H) ppm.

In the first step of Reaction Scheme II, 3-amino-N-(4-chloro-3-(trifluoromethyl)phenyl)-4-methylbenzamide is synthesized. In this step, 1 equivalent of 4-chloro-3-(trifluoromethyl)aniline and 1.2 equivalents of triethylamine are dissolved in 3 ml of dichloromethane. The mixture is placed in ice bath and 3 ml of 4-Methyl-3-nitrobenzoyl chloride (0.28 mmol, dissolved in dichloromethane) was added slowly, followed by stirring at room temperature for 3 hours. Next, in the presence of hydrogen gas and palladium, the nitro group of the crude intermediate is reduced to an amine group, and the mixture is filtered and purified by column chromatography (hexane/ethyl acetate=9:1) to obtain 3-amino-N-(4).

3-amino-N-(4-chloro-3-(trifluoromethyl)phenyl)-4-methylbenzamide 1H NMR (400 MHz, MeOH): δ 8.24 (s, 1H), 7.95 (d, J=8.8 Hz, 1H), 7.57 (d, J 8.8 Hz, 1H), 7.25 (s, 1H), 7.16 (q, J=8.0 Hz, 2H), 2.22 (s, 3H) ppm. HRMS calculated for C15H12 ClF3N2O (M−H)—: 328.72. Found: 327.22.

In the final step of Scheme II, the final product compound SCT-1001 is synthesized. First, 1.0 equivalent of 4-(2-chloropyrimidin-4-yl)benzonitrile and 0.61 mmol of 3-amino-N-(4-chloro-3-(trifluoromethyl)phenyl)-4-methylbenzamide are mixed in isopropyl alcohol (IPA) and a catalytic amount of HCl is added. Next, the mixture is In the first step of the above reaction formula III, the compound I and the compound B are subjected to a coupling reaction in the presence of THF to obtain an intermediate compound J. Triphosgene and THF are first added to the THF solution containing Compound I and TEA at 4° C. Then, Compound B was added to obtain a mixed solution, which was then stirred at 4° C. for 5 minutes. The reaction is carried out for 3 hours at room temperature, and then ice water is added to quench the reaction. The reaction mixture is extracted with 100 ml of ethyl acetate to obtain an organic layer. The organic layer is washed with brine and then dehydrated with anhydrous magnesium sulfate (MgSO$_4$) and filtered. The filtered solution is concentrated and purified by column chromatography to obtain an intermediate Compound J. The intermediate Compound J is subjected to a hydration reaction in the presence of hydrogen and Palladium/charcoal. The mixture is filtered and purified by column chromatography to obtain compound K. On the other hand, compound E is coupled with substituted boronic acid F in the presence of Pd(dppf)$_2$Cl$_2$ to obtain compound G. In this reaction, Compound E (dissolved in DME, dehydrated) is mixed with boronic acid F and Pd(dppf)$_2$Cl$_2$ and heated to 90° C. in nitrogen. The solution is cooled to room temperature, filtered, concentrated and purified by chromatography column to obtain compound. G. In the final step, the compound G and the compound K are coupled in isopropanol alcohol (IPA) by adding a catalytic amount of hydrochloric acid (HCl). The mixture was heated at 100° C. for 8 hours, extracted with 100 ml of ethyl acetate, and the obtained organic layer was washed with brine, dried over anhydrous magnesium sulfate (MgSO$_4$), and filtered. The filtered solution is then concentrated and purified by column chromatography to obtain compound H.

In the above Scheme III, R$_1$ is an unsubstituted or substituted aromatic ring group, for example, an unsubstituted or substituted phenyl group or a substituted

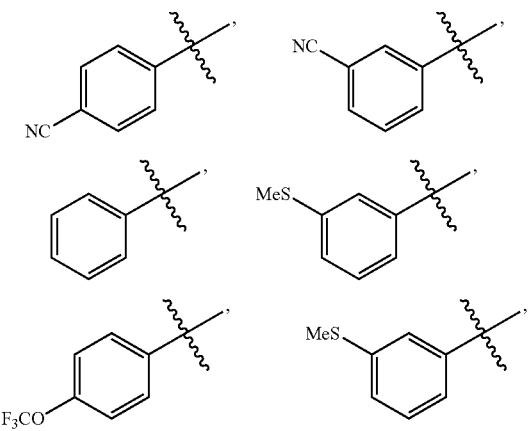

an unsubstituted pyrrolic group, a substituted pyrrolic group, a substituted

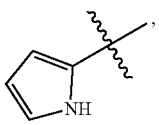 [SMILES: *c1ccc[nH]1]

an unsubstituted thiophene group, a substituted thiophene group, a substituted

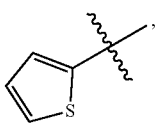 [SMILES: *c1cccs1]

an unsubstituted naphthalenic group, a substituted naphthalenic group, a substituted

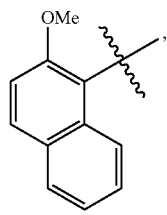 [SMILES: *c1c(OC)ccc2ccccc12]

a di-substituted phenyl group, a substituted

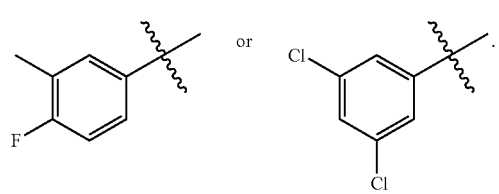

Further, in the above Scheme III, R$_3$ may be a substituted phenyl amide, such as a substituted

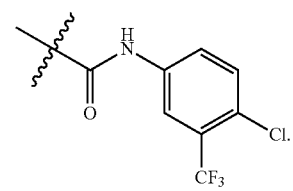

R$_3$ may be a substituted phenyl urea group, such as a substituted

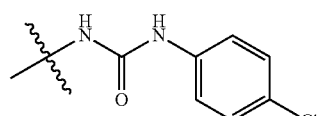

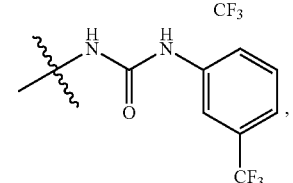

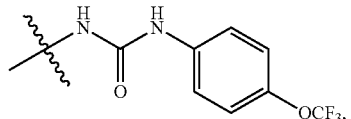

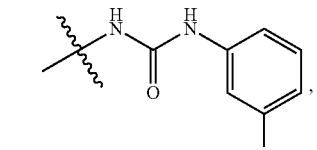

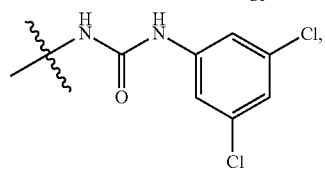

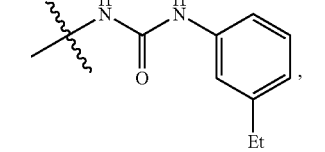

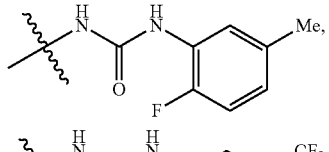

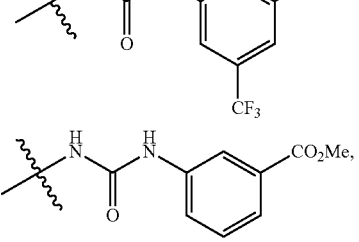

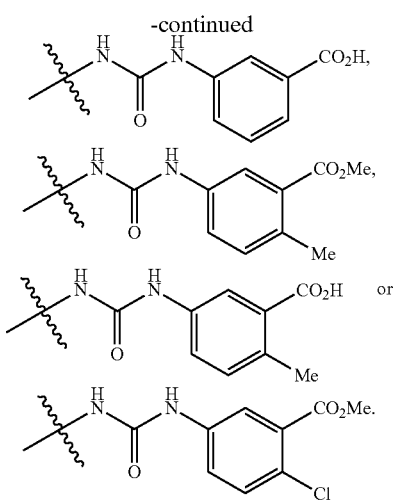

Further, in the above Scheme III, Ar may be an unsubstituted or substituted phenyl group, for example:

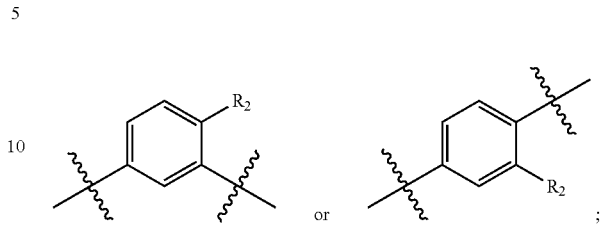

wherein, $R_2$ may be a hydrogen atom, a halide or an alkyl group. In some preferred embodiments, the halide is fluoride or chloride, and the alkyl group is methyl group or ethyl group.

The derivatives as listed in Table 2 can be synthesized by the above Scheme III.

TABLE 2

| SCT | $R_1$ | $R_2$ | $R_3$ |
|---|---|---|---|
| 1013 | 4-NC-phenyl | H | urea-(4-Cl-3-CF$_3$-phenyl) |
| 1014 | 3-NC-phenyl | H | urea-(4-Cl-3-CF$_3$-phenyl) |
| 1015 | 2-pyrrolyl (NH) | H | urea-(4-Cl-3-CF$_3$-phenyl) |
| 1016 | phenyl | H | urea-(4-Cl-3-CF$_3$-phenyl) |
| 1017 | 2-thienyl | H | urea-(4-Cl-3-CF$_3$-phenyl) |

TABLE 2-continued
the derivatives of the present invention
| SCT | R₁ | R₂ | R₃ |
|---|---|---|---|
| 1018 | 3-(MeS)phenyl | H | -NHC(O)NH-(4-Cl-3-CF₃-phenyl) |
| 1019 | 4-F-3-Me-phenyl | H | -NHC(O)NH-(4-Cl-3-CF₃-phenyl) |
| 1020 | 4-(F₃CO)phenyl | H | -NHC(O)NH-(4-Cl-3-CF₃-phenyl) |
| 1021 | 4-(F₃C)phenyl | H | -NHC(O)NH-(4-Cl-3-CF₃-phenyl) |
| 1023 | 3,5-diCl-phenyl | H | -NHC(O)NH-(4-Cl-3-CF₃-phenyl) |
Embodiment 1 Synthesis of Compound SCT-1001
SCT-1015 is Synthesized by the Following Scheme IV:
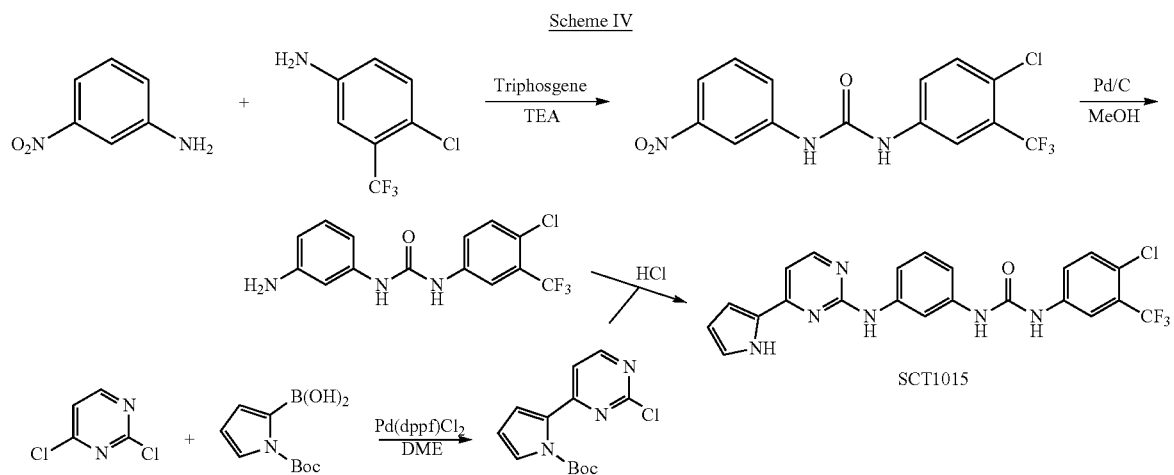
Scheme IV First, 0.148 g, 0.61 mmol of chloro-3-(trifluoromethyl) aniline and 2.2 mmol of triethylamine are mixed in 3 ml of dry THF and then 0.30 mmol triphosgene (dissolved in dry THF) is slowly added to the mixture in an ice bath. The mixture is stirred at room temperature for 30 minutes, then concentrated, and 1 equivalent of 3-nitroaniline is added to react at 65° C. for 30 minutes, and then concentrated again. The crude intermediate is then converted to an amine intermediate by a catalyst Pd/C, then filtered and purified by column chromatography (hexane/ethyl acetate=1:1) to obtain 1-(3-aminophenyl)-3-(4-chloro-3-(trifluoromethyl) phenyl)urea.

1-(3-aminophenyl)-3-(4-chloro-3-(trifluoromethyl)phenyl)urea 1H NMR (400 MHz, MeOD-d 4): δ 7.98 (d, J=2.4 Hz, 1H), 7.60 (dd, J=8.8, 2.4 Hz, 1H), 7.49 (d, J=8.8 Hz, 1H), 7.02 (t, J=8.0 Hz, 1H), 6.91 (s, 1H), 6.70 (dd, J=8.0, 1.2 Hz, 1H), 6.44 (dd, J=8.0, 1.2 Hz, 1H) ppm.

In the second step of Scheme IV, the intermediate t-butyl-2-(2-chloropyrimidin-4-yl)-1H-pyrrole-1-carboxylate is synthesized. 2,4-dichloropyrimidine (dissolved in dimethoxy ethane), 1-(tert-butoxycarbonyl)-1H-pyrrol-2-yl-pyrrol) boronic acid and a catalytic amount of 1'-Bis(diphenylphosphino)ferrocene)palladium(II) dichloride, Pd(dppf)Cl$_2$ are mixed with 3 equivalents of triethylamine, and the mixture is heated at 90° C. for 3 hours, and then filtered, purified by column chromatography (hexane/ethyl acetate=9:1) to obtain t-butyl 2-(2-chloropyrimidin-4-yl)-1H-pyrrole-1-carboxylate.

Tert-butyl 2-(2-chloropyrimidin-4-yl)-1H-pyrrole-1-carboxylate 1H NMR (400 MHz, CDCl3): δ 8.47 (d, J=5.2 Hz, 1H), 7.36 (dd, J=3.6, 2.0 Hz, 1H), 7.28 (d, J=5.2 Hz, 1H), 6.64 (dd, J=3.6, 1.6 Hz, 1H), 6.20 (t, J=3.6 Hz, 1H), 1.40 (s, 9H) ppm.

In the final step of Scheme IV, the final product compound SCT-1015 is synthesized. First, 1.0 equivalent of t-butyl 2-(2-chloropyrimidin-4-yl)-1H-pyrrole-1-carboxylate and 0.61 mmol of 1-(3-aminophenyl)-3-(4-chloro-3-(Trifluoromethyl)phenyl)urea are mixed in isopropyl alcohol (IPA) and added with a catalytic amount of HCl. Next, the mixture was concentrated and purified by column chromatography (hexane/ethyl acetate=2:1) to obtain 1-(3-((4-(1H-pyrrol-2-yl)pyrimidin-2-yl)amino)phenyl)-3-(4-chloro-3-(trifluoromethyl)phenyl)urea, which is the compound SCT-1015.

1-(3-((4-(1H-pyrrol-2-yl)pyrimidin-2-yl)amino)phenyl)-3-(4-chloro-3-(trifluoromethyl)phenyl)urea 1H NMR (400 MHz, DMSO-d 6): δ 11.75 (s, 1H), 10.55 (s, 1H), 9.91 (s, 1H), 9.61 (s, 1H), 8.45 (s, 1H), 8.35 (d, J=6.4 Hz, 1H), 8.08 (s, 1H), 7.64 (s, 2H), 7.38 (s, 1H), 7.34 (d, J=6.4 Hz, 1H), 7.28 (t, J=8.0 Hz, 1H), 7.22 (s, 1H), 7.12 (d, J=8.0 Hz, 1H), 7.03 (d, J=7.6 Hz, 1H), 6.36 (s, 1H) ppm. 13C NMR (100 MHz, DMSO-d6): δ 159.5, 153.1, 152.3, 148.3, 139.2, 138.8, 137.8, 131.6, 128.8, 127.9, 126.8, 126.3 (q), 122.5, 122.3 (q), 121.9, 116.7, 116.1 (q), 113.7, 113.1, 111.4, 109.8, 104.7 ppm. HRMS calculated for C$_{22}$H$_{16}$ClF$_3$N$_6$O (M−H)$^-$:471.0942. Found: 471.0957.

The Compounds of the Invention and Derivatives Thereof

Embodiment 1 N-(4-chloro-3-(trifluoromethyl)phenyl)-3-((4-(4-cyanophenyl)pyrimidin-2-yl)amino)-4-methylbenzamide (Compound SCT-1001)

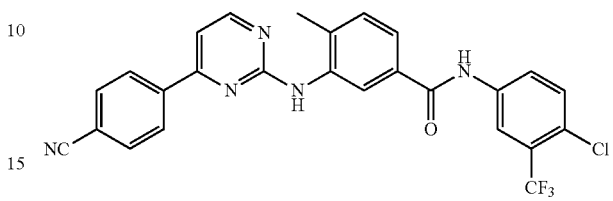

SCT1001

$^1$H NMR (400 MHz, CDCl3): δ 8.79 (s, 1H), 8.53 (d, J=5.2 Hz, 1H), 8.23 (s, 1H), 8.17 (d, J=8.4 Hz, 2H), 7.90~7.87 (m, 2H), 7.74 (d, J=8.4 Hz, 2H), 7.47 (t, J=8.0 Hz, 2H), 7.30 (d, J=8.0 Hz, 1H), 7.19 (d, J=5.2 Hz, 1H), 7.12 (s, 1H), 2.40 (s, 3H ppm. HRMS calculated for C$_{26}$H$_{17}$ClF$_3$N$_5$O (M−H)$^-$: 506.0990. Found: 506.1010.

Embodiment 2 N-(4-chloro-3-(trifluoromethyl)phenyl)-3-((4-(3-cyanophenyl)pyrimidin-2-yl)amino)-4-methylbenzamide (Compound SCT-1002)

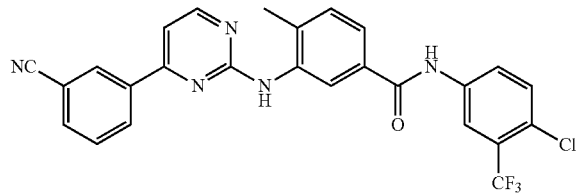

SCT1002

$^1$H NMR (400 MHz, CDCl 3): δ 8.88 (s, 1H), 8.56 (d, J=5.2 Hz 1H), 8.41 (s, 1H), 8.32 (d, J=8.0 Hz, 1H), 8.00 (s, 1H), 7.95 (dd J=8.4, 2.8 Hz, 1H), 7.87 (s, 1H), 7.76 (d, J=8.0 Hz, 1H), 7.59 (t, J=8.0 Hz, 1H), 7.51~7.48 (m, 2H), 7.30 (d, J=7.6 Hz, 1H), 7.20 (d, J=5.2 Hz, 1H), 7.09 (s, 1H), 2.44 (s, 3H) ppm. 13 C NMR (100 MHz, DMSO-d6): δ 164.9, 160.9, 160.4, 159.4, 138.2, 137.6, 137.2, 135.9, 133.7, 131.4, 131.3, 130.8, 130.0, 129.9, 129.6, 126.0 (q), 124.4, 123.6, 122.9, 120.9, 118.5 (q), 117.9, 111.6, 107.4, 17.7 ppm. HRMS calculated for C$_{26}$H$_{17}$ClF$_3$N$_5$O (M−H)$^-$506.0990. Found: 506.1008.

Embodiment 3 3-((4-(1H-pyrrol-2-yl)pyrimidin-2-yl)amino)-N-(4-chloro-3-(trifluoromethyl)phenyl)-4-methylbenzamide (Compound SCT-1003)

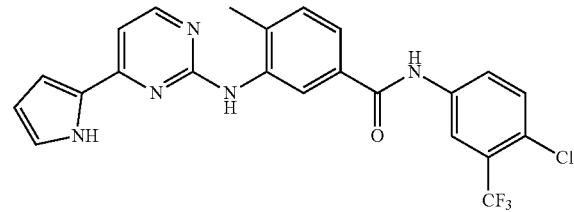

SCT1003

¹H NMR (400 MHz, MeOD-d4): δ 8.43 (d. J=2.0 Hz, 1H), 8.26 (d, J=2.4 Hz, 1H), 8.19 (d, J=5.6 Hz, 1H), 7.96 (dd, J=8.8, 2.4 Hz, 1H), 7.63 (dd, J=8.0, 2.0 Hz, 1H), 7.58 (d, J=8.8 Hz, 1H), 7.40 (d, J=8.0 Hz, 1H), 7.02 (d, J=5.6 Hz, 1H), 6.99 (dd, J=2.8, 1.6 Hz, 1H) 6.95 (dd, J=3.6, 1.6 Hz, 1H), 6.25 (dd, J=3.6, 2.8 Hz, 1H), 2.41 (s, 3H) ppm. HRMS calculated for $C_{23}H_{17}ClF_3N_5O$ (M–H)⁻: 470.0990. Found: 470.0997.

Embodiment 4 N-(4-chloro-3-(trifluoromethyl)phenyl)-4-methyl-3-((4-phenylpyrimidin-2-yl)amino)benzamide (Compound SCT-1004)

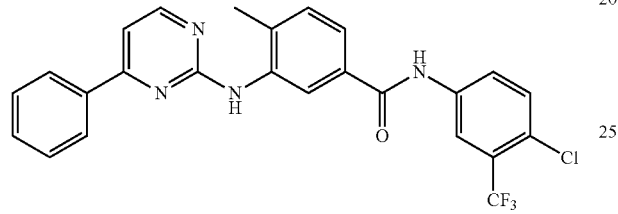

SCT1004

¹H NMR (400 MHz, MeOD-d4): δ 8.46 (d. J=6.4 Hz, 1H), 8.36 (s, 1H), 8.30 (s, 1H), 8.29 (d, J=7.2 Hz, 2H), 8.08 (dd, J=8.8, 2.8 Hz, 1H), 7.99 (dd, 8.0, 1.6 Hz, 1H), 7.75 (d. J=6.4 Hz, 1H), 7.71 (t, J=6.4 Hz, 1H), 7.66~7.59 (m, 4H), 2.48 (s, 3H) ppm, 13 C NMR (100 MHz, MeOD-d4): δ 172.4, 167.2, 156.0, 150.0, 140.2, 139.7, 135.8, 134.8, 133.1, 132.7, 130.5, 129.7, 129.0 (q), 127.9, 127.1, 127.0, 126.2, 124.3 (q), 120.5 (q), 108.7, 18.4 ppm. HRMS calculated for $C_{25}H_{18}ClF_3N_4O$ (M–H)⁻: 481.1038. Found: 481.1043.

Embodiment 5 N-(4-chloro-3-(trifluoromethyl)phenyl)-3-((4-(2-methoxynaphthalen-1-yl)pyrimidin-2-yl)amino)-4-methylbenzamide (Compound SCT-1005)

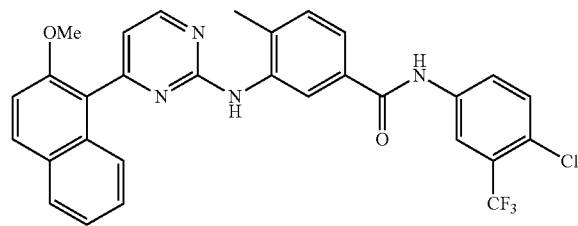

SCT1005

¹H NMR (400 MHz, MeOD-d4): δ 8.49 (d, J=5.2 Hz, 1H), 8.30 (s, 1H), 8.13 (d, 1H), 7.95 (d, J=9.2 Hz, 1H), 7.78 (d, J=8.0 Hz, 2H), 7.56~7.52 (m, 3H), 7.44 (d, J=9.2 Hz, 1H), 7.37~7.32 (m, 2H), 7.24 (t, J=7.6 Hz, 1H), 6.91 (d, J=5.2 Hz, 1H), 3.87 (s, 3H), 2.38 (s, 3H) ppm. HRMS calculated for $C_{30}H_{22}ClF_3N_4O_2$(M–H)⁻: 561.1300. Found: 561.1311.

Embodiment 6 N-(4-chloro-3-(trifluoromethyl)phenyl)-4-methyl-3-((6-phenylpyrimidin-4-yl)amino)benzamide, (Compound SCT-1006)

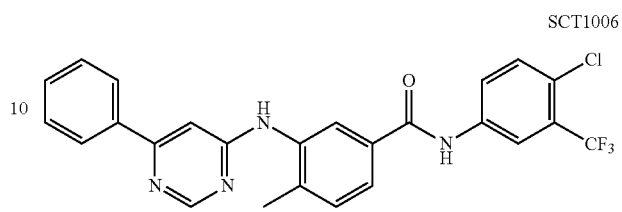

SCT1006

¹H NMR (400 MHz, MeOD-d4): δ 8.76 (s, 1H), 8.27 (d, J=24 Hz, 1H), 8.05 (s, 1H), 7.97 (dd, J=8.8, 2.4 Hz, 1H), 7.94 (dd, J=8.0, 2.0 Hz, 1H), 7.85 (d, J=7.6 Hz, 2H), 7.73~7.56 (m, 5H), 7.11 (s, 1H), 2.42 (s, 3H) ppm. 13 C NMR (100 MHz, MeOD-d4): δ 166.2, 163.6, 154.5, 152.4, 139.0, 138.0, 134.9, 133.1, 132.6, 131.6, 131.3, 130.1, 129.5, 127.9 (q), 127.1, 126.7, 126.1, 125.9, 124.8, 124.2, 121.5, 119.3 (q), 16.8 ppm. HRMS calculated for $C_{25}H_{18}ClF_3N_4O$ (M–H)—: 481.1038. Found: 481.1043.

Embodiment 7 N-(4-chloro-3-(trifluoromethyl)phenyl)-4-methyl-3-((4-(thiophen-2-yl)pyrimidin-2-yl)amino)benzamide (Compound SCT-1007)

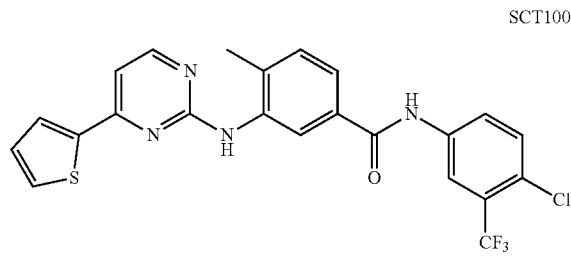

SCT1007

¹H NMR (400 MHz, MeOD-d4): δ 10.7 (s, 1H), 9.86 (s, 1H), 8.45 (d, J=5.6 Hz, 1H), 8.37 (d, J=2.4 Hz 1H), 8.24 (s, 1H), 8.15 (dd, J=8.8, 2.4 Hz, 1H), 8.12 (d, J=4.0 Hz, 1H), 7.86 (d, J=4.0 Hz, 1H), 7.82 (d, J=8.0 Hz, 1H), 7.69 (d, J=8.0 Hz, 1H), 7.48~7.45 (m, 2H), 7.25 (dd, J=4.8, 4.0 Hz, 1H), 2.35 (s, 3H) ppm. 13 C NMR (100 MHz, DMSO-d6): δ 165.0, 161.2, 156.8, 153.3, 140.9, 138.3, 136.8, 135.9, 132.8, 131.8, 131.5, 130.3, 130.2, 128.7, 126.1 (q), 124.5, 124.4, 124.3, 123.7, 120.9, 118.5 (q), 105.6, 17.7 ppm. HRMS calculated for $C_{23}H_{16}ClF_3N_4OS$ (M–H)⁻: 487.0602. Found: 487.0609.59.

Embodiment 8 N-(4-chloro-3-(trifluoromethyl)phenyl)-4-methyl-3-((4-(3-(methylthio)phenyl)pyrimidin-2-yl)amino)benzamide (Compound SCT-1008)

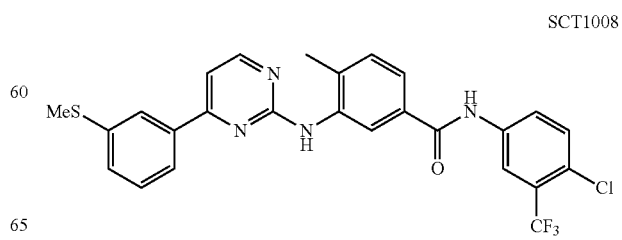

SCT1008

¹H NMR (400 MHz, DMSO-d6): δ 10.7 (s, 1H), 9.70 (s, 1H), 8.56 (d, J=5.6 Hz, 1H), 8.40 (s, 1H), 8.34 (s, 1H), 8.15 (d, J=8.8 Hz, 1H), 7.97 (s, 1H), 7.89 (d, J=6.0 Hz, 1H), 7.81 (d, J=8.0 Hz, 1H), 7.69 (d, J=8.8 Hz, 1H), 7.55 (d, J=5.6 Hz, 1H), 7.46-7.41 (m, 3H), 2.42 (s, 3H), 2.36 (s, 3H) ppm. 13 C NMR (100 MHz, DMSO-d6): δ 165.0, 164.5, 158.0, 155.6, 138.9, 138.3, 136.5, 136.4, 135.9, 131.6, 131.5, 130.1, 129.0, 128.3, 126.1 (q), 124.5, 124.0, 123.8, 123.7, 123.6, 123.3, 121.0, 118.5 (q), 107.3, 17.7, 13.9 ppm. HRMS calculated for $C_{26}H_{20}ClF_3N_4OS(M-H)^-$: 527.0915. Found: 527.0922.

Embodiment 9 N-(4-chloro-3-(trifluoromethyl)phenyl)-3-((4-(4-fluoro-3-methylphenyl)pyrimidin-2-yl)amino)-4-methylbenzamide (Compound SCT-1009)

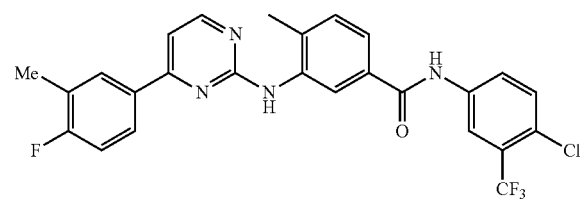

SCT1009

¹H NMR (400 MHz, DMSO-d6): δ 10.69 (s, 1H) 9.52 (s, 1H), 8.53 (d, J=5.6 Hz, 1H), 8.48 (s, 1H), 8.42 (d, J=2.4 Hz, 1H), 8.18 (d, J=6.4 Hz, 1H), 8.12 (d, J=8.8 Hz, 1H), 8.03~8.00 (m, 1H), 7.78 (d, J=8.0 Hz, 1H), 7.69 J=8.8 Hz, 1H), 7.50 (d, J=5.6 Hz, 1H), 7.43 (d, J=8.0 Hz, 1H), 7.24 (t, J=8.8 Hz, 1H), 2.37 (s, 3H), 2.26 (s, 3H) ppm. 13 C NMR (100 MHz DMSO-d6): δ 166.1, 164.9, 164.6, 162.1, 159.0, 156.7, 139.3, 137.7, 136.5, 132.4, 131.5 (d), 130.9, 127.6 (d), 126.9 (q), 125.6, 125.4, 125.3, 124.6, 124.4, 124.1, 121.9, 119.3 (q), 116.0 (d), 108.0, 18.6, 14.5 (d) ppm. HRMS calculated for $C_{26}H_{19}ClF_4N_4O(M-H)^-$ 513.1100. Found: 513.1106.

Embodiment 10 N-(4-chloro-3-(trifluoromethyl)phenyl)-4-methyl-3-((4-(4-(trifluoromethoxy)phenyl)pyrimidin-2-yl)amino)benzamide (Compound SCT-1010)

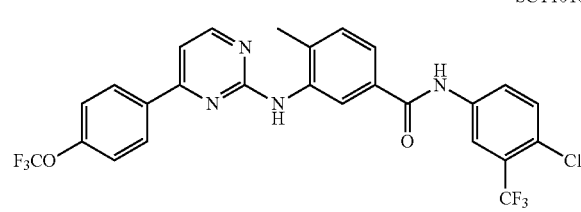

SCT1010

¹H NMR (400 MHz, MeOD-d4): δ 8.45 (d, J=6.4 Hz, 1H), 8.40 (d, J=8.4 Hz, 2H), 8.33 (s, 1H), 8.27 (s, 1H), 8.02 (d, J=9.2 Hz, 1H), 7.97 (d, J=8.0 Hz, 1H), 7.73 (d, J=6.4 Hz, 1H), 7.61 (d, J=8.4 Hz, 2H), 7.49 (d, J=8.4 Hz, 2H), 2.47 (s, 3H), ppm. 13C NMR (100 MHz, MeOD-d4): δ 171.2, 167.4, 156.1, 154.1, 150.1, 140.3, 139.5, 135.6, 134.8, 134.5, 133.1, 132.8, 131.9, 129.0 (m), 128.0, 127.2, 127.0, 126.1, 125.6, 123.0, 122.9, 122.3, 120.6 (m), 120.4, 108.7, 18.2 ppm. HRMS calculated for $C_{26}H_{17}ClF_6N_4O_2(M-H)^-$: 565.0860. Found: 565.0864.

Embodiment 11 N-(4-chloro-3-(trifluoromethyl)phenyl)-4-methyl-3-((4-(4-(trifluoromethyl)phenyl)pyrimidin-2-yl)amino)benzamide (Compound SCT-1011)

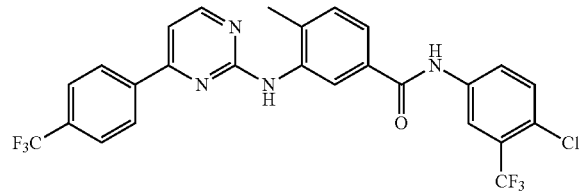

SCT1011

¹H NMR (400 MHz, MeOD-d4): δ 8.45~8.41 (m, 3H), 8.27 (d, J=8.4 Hz, 2H), 7.97 (d, J=9.2 Hz, 1H), 7.92 (d, J=7.6 Hz, 1H), 7.87 (d, J=8.4 Hz, 2H), 7.70 (d, J=6.4 Hz, 1H), 7.59 (t, J=7.6 Hz, 2H), 2.46 (s, 3H) ppm. HRMS calculated for $C_{26}H_{17}ClF_6N_4O(M-H)^-$: 549.0911. Found: 549.0916.

Embodiment 12 N-(4-chloro-3-(trifluoromethyl)phenyl)-3-((4-(3,5-dichlorophenyl)pyrimidin-2-yl)amino)-4-methylbenzamide (Compound SCT-1012)

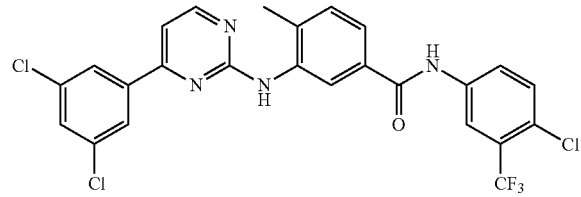

SCT1012

¹H NMR (400 MHz, DMSO-d6): δ 10.64 (s, 1H), (s, 1H), 8.56 (d, J=5.2 Hz, 1H), 8.41 (s, 1H), 8.39 (s, 1H), 8.16 (s, 2H), 8.11 (d, J=8.8 Hz, 1H), 7.76~7.74 (m, 2H), 7.69 (d, J=8.8 Hz, 1H), 7.55 (d, J=5.2 Hz, 1H), 7.41 (d, J=8.0 Hz, 1H), 2.35 (s, 3H) ppm, 13 C NMR (100 MHz, DMSO-d6): δ 165.0, 160.6, 159.7, 158.7, 139.4, 138.4, 137.2, 135.7, 134.3, 131.4, 131.3, 129.9, 129.8, 126.0 (q), 125.2, 124.5, 123.6, 123.1, 122.3, 121.0, 118.5 (q), 107.7, 17.7 ppm. HRMS calculated for $C_{25}H_{16}Cl_3F_3N_4O(M-H)^-$: 549.0258. Found: 549.0270.

Embodiment 13 1-(4-chloro-3-(trifluoromethyl)phenyl)-3-(3-((4-(4-cyanophenyl)pyrimidin-2-yl)amino)phenyl)urea (Compound SCT-1013)

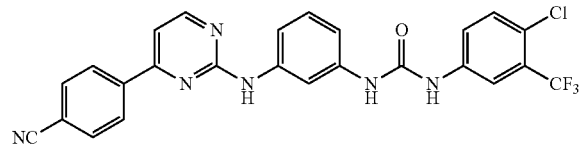

SCT1013

¹H NMR (400 MHz, DMSO-d6): δ 9.76 (s, 1), 9.57 (s, 1H), 9.08 (s, 1H), 8.62 (d, J=5.2 Hz, 1H), 8.44 (d, J=8.0 Hz, 2H), 8.21 (s, 1H), 8.18 (s, 1H), 7.96 (d, J=8.0 Hz, 2H), 7.60 (s, 2H), 7.51 (d, J=5.2 Hz, 1H), 7.32 (d, J=8.0 Hz, 1H), 7.20 (t, J=8.0 Hz, 1H), 7.04 (d, J=6.8 Hz, 1H) ppm. 13 C NMR (100 MHz, DMSO-d6): δ 161.2, 159.6, 159.1, 151.9, 140.3, 139.1, 139.0, 132.3, 131.5, 128.3, 127.4, 126.2 (q), 123.7, 122.3, 121.6, 121.0, 118.0, 115.9 (q), 112.9, 112.6, 111.5, 108.6, 108.0 ppm. HRMS calculated for $C_{25}H_{16}ClF_3N_6O$ (M−H)⁻: 507.0942. Found: 507.0955.

Embodiment 14 1-(4-chloro-3-(trifluoromethyl)phenyl)-3-(3-(4-(3-cyanophenyl)pyrimidin-2-yl)amino)phenyl)urea (Compound SCT-1014)

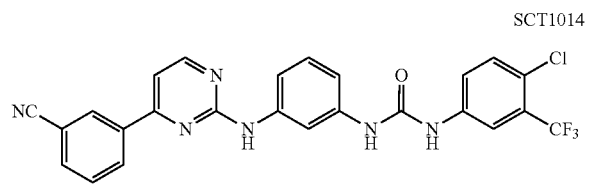 [SMILES: N#Cc1cccc(-c2ccnc(Nc3cccc(NC(=O)Nc4ccc(Cl)c(C(F)(F)F)c4)c3)n2)c1]

SCT1014

¹H NMR (400 MHz, MeOD-d4): δ 8.66 (s, 1H), 8.59 (d, J=8.8 Hz, 1H) 8.47 (d, J=6.4 Hz, 1H), 8.19 (s, 1H), 8.04 (d, J=2.4 Hz, 1H), 7.96 (d, J=8.0 Hz, 1H), 7.75 (t, J=8.0 Hz, 1H), 7.64 (d, J=6.0 Hz, 1H), 7.61 (dd, J=8.8, 2.4 Hz, 1H), 7.49 (d, J=8.4 Hz, 1H), 7.39 (t, J=8.0 Hz, H), 7.22 (d, J=8.0 Hz, 1H), 7.15 (d, J=8.0 Hz, 1H) ppm. HRMS calculated for $C_{25}H_{16}ClF_3N_6O$(M−H)⁻: 507.0942. Found: 507.0954.

Embodiment 15 1-(3-((4-(1H-pyrrol-2-yl)pyrimidin-2-yl)amino)phenyl)-3-(4-chloro-3-(trifluoromethyl)phenyl)urea (Compound SCT-1015)

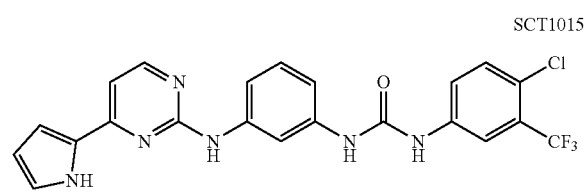 [SMILES: O=C(Nc1cccc(Nc2nccc(-c3ccc[nH]3)n2)c1)Nc1ccc(Cl)c(C(F)(F)F)c1]

SCT1015

¹H NMR (400 MHz, DMSO-d6): δ 11.75 (s, 1H), 10.55 (s, 1H), 9.91 (s, 1H), 9.61 (s, 1H), 8.45 (s, 1H), 8.35 (d, J=6.4 Hz, 1H), 8.08 (s, 1H), 7.64 (s, 2H), 7.38 (s, 1H), 7.34 (d, J=6.4 Hz, 1 Hz, 1H), 7.28 (t, J=8.0 Hz, 1H), 7.22 (s, 1H), 7.1 (d, J=8.0 Hz, 1H), 7.03 (d, J=7.6 Hz, 1H), 6.36 (s, 1H) ppm. 13 C NMR (100 MHz, DMSO-d6): δ 159.5, 153.1, 152.3, 148.3, 139.2, 138.8, 137.8, 131.6, 128.8, 127.9, 126.8, 126.3 (q), 122.5, 122.3 (q), 121.9, 116.7, 116.1 (q), 113.7, 113.1, 111.4, 109.8, 104.7 ppm. HRMS calculated for $C_{22}H_{16}ClF_3N_6O$(M−H)⁻: 471.0942. Found: 471.0957.

Embodiment 16 1-(4-chloro-3-(trifluoromethyl)phenyl)-(3-((4-phenylpyrimidin-2-yl)amino)phenyl)urea (Compound SCT-1016)

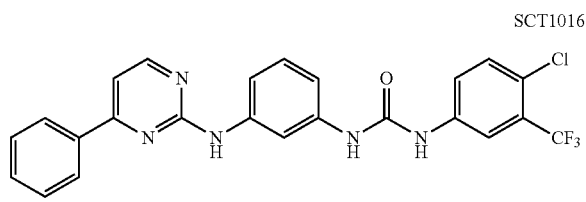 [SMILES: O=C(Nc1cccc(Nc2nccc(-c3ccccc3)n2)c1)Nc1ccc(Cl)c(C(F)(F)F)c1]

SCT1016

¹H NMR (400 MHz DMSO-d6): δ 10.00 (s, 1H), 9.85 (s, 1H), 9.31 (s, 1H), 8.56 (d, J=5.6 Hz, 1H), 8.28~8.26 (8.17 (s, 1H), 8.14 (s, 1H), 7.62 (s, 2H), 7.54~7.53 (m, 3H), 7.49 (d, J=5.6 Hz, 1H), 7.37 (d, J=8.0 Hz, 1H), 7.24 (t, J=8.0 Hz, 1H), 7.08 (d, J=8.0 Hz, 1H) ppm. 13 C NMR (100 MHz, DMSO-d6): δ 164.5, 158.1, 156.4, 152.0, 139.7, 139.2, 139.1, 135.6, 131.6, 130.9, 128.5, 128.4, 127.0, 126.3 (q), 122.4 (q), 122.2, 121.5, 115.8 (q), 113.3, 112.0, 109.2, 107.3 ppm. HRMS calculated for $C_{24}H_{17}ClF_3N_5O$(M−H)⁻: 482.0990. Found: 482.1002.

Embodiment 17 1-(4-chloro-3-(trifluoromethyl)phenyl)-3-(3-((4-(thiophen-2-yl)pyrimidin-2-yl)amino)phenyl)urea (Compound SCT-1017)

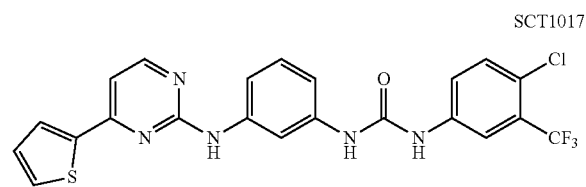 [SMILES: O=C(Nc1cccc(Nc2nccc(-c3cccs3)n2)c1)Nc1ccc(Cl)c(C(F)(F)F)c1]

SCT1017

¹H NMR (400 MHz, MeOD-d4): δ 8.23 (d, J=6.4 Hz, 1H), 8.18 (d, J=4.0 Hz, 1H), 8.03 (d, J=2.4 Hz, 1H), 7.94 (d, J=4.0 Hz, 1H), 7.91 (s, 1H), 7.63 (dd, J=8.4, 2.4 Hz, 1H), 7.51 (d, J=7.6 Hz, 1H), 7.50 (d, J=6.8 Hz, 1H), 7.43 (t, J=8.4 Hz, 1H), 7.31~27.24 (m, 3H) ppm. 13 C NMR (100 MHz, DMSO-d6): δ 160.3, 156.9, 154.7, 152.0, 141.2, 139.1, 139.1, 132.1, 131.5, 129.7, 128.5, 128.5, 126.2 (q), 122.2, 121.6, 121.0 (q), 115.8 (q), 113.7, 112.7, 109.8, 105.8 ppm. HRMS calculated for $C_{22}H_{15}ClF_3N_5OS$(M−H)⁻: 488.0554. Found: 488.0568.

Embodiment 18 1-(4-chloro-3-(trifluoromethyl)phenyl)-3-(3-((4-(3-(methylthio)phenyl)pyrimidin-2-yl)amino)phenyl)urea (Compound SCT-1018)

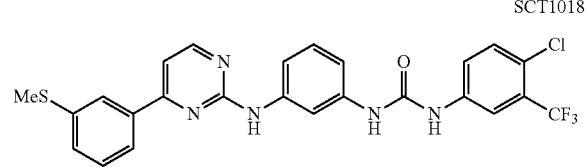 [SMILES: CSc1cccc(-c2ccnc(Nc3cccc(NC(=O)Nc4ccc(Cl)c(C(F)(F)F)c4)c3)n2)c1]

SCT1018

¹H NMR (400 MHz, MeOD-d4): δ 8.37 (d, 6.8 Hz, 1H), 8.18 (s, 1H), 8.05~8.04 (m, 3H), 7.67 (d, J=6.4 Hz, 1H) 7.62

(dd, J=8.8, 2.4 Hz, 1H), 7.55~7.48 (m, 3H), 7.44 (t, J=8.0 Hz, 1H), 7.24 (t, J=8.0 Hz, 2H), 2.53 (s, 3H) ppm, 13 C NMR (100 MHz, DMSO-d6): δ 163.5, 158.5, 157.1, 152.0, 139.8, 139.1, 138.7, 136.4, 131.5, 129.0, 128.3, 128.0, 126.4 (q), 123.6, 123.3, 122.3 (q), 122.2, 121.5, 115.9 (q), 113.3, 112.0, 109.3, 107.5, 14.0 ppm. HRMS calculated for $C_{25}H_{19}ClF_3N_5OS(M-H)^-$: 528.0867. Found: 528.0878.

Embodiment 19 1-(4-chloro-3-(trifluoromethyl)phenyl)-3-(3-((4-(4-fluoro-3-methylphenyl)pyrimidin-2-yl)amino)phenyl)urea (Compound SCT-1019)

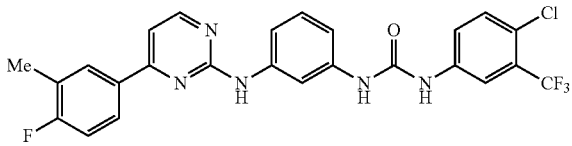

¹H NMR (400 MHz, DMSO-d6): δ 9.90 (s, 1H), 9.75 (s, 1H), 9.25 (s, 1H), 8.54 (d, J=5.6 Hz, 1H), 8.19~8.13 (m, 4H), 7.60 (s, 1H), 7.59 (s, 1H), 7.45 (d, J=5.6 Hz, 1H), 7.32~7.20 (m, 3H), 7.04 (d, J=8.0 Hz, 1H), 2.27 (s, 3H) ppm. 13 C NMR (100 MHz, DMSO-d6): δ 163.4, 163.3, 161.0, 158.3, 156.8, 152.0, 139.8, 139.1, 131.8 (d), 131.5, 130.4 (d), 128.3, 126.8 (d), 126.2 (q), 124.4 (d), 122.3 (q), 122.2, 121.6, 115.9 (q), 115.0 (d), 113.2, 111.9, 109.2, 107.1, 13.7 (d) ppm. HRMS calculated for $C_{25}H_{16}ClF_4N_5O(M-H)^-$: 514.1052. Found: 514.1062.

Embodiment 20 1-(4-chloro-3-(trifluoromethyl)phenyl)-3-(3-((4-(4-(trifluoromethoxy)phenyl)pyrimidin-2-yl)amino)phenyl)urea (Compound SCT-1020)

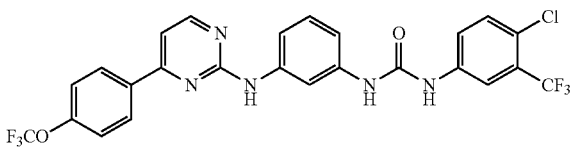

¹H NMR (400 MHz, DMSO-d6): δ 9.83 (s, 1H), 9.72 (s, 1H), 9.20 (s, 1H), 8.58 (d, J=5.6 Hz, 1H), 8.41 (d, J=9.2 Hz, 2H), 8.30 (s, 1H), 8.19 (s, 1H), 7.60 (s, 1H), 7.59 (s, 1H), 7.46 (d, J=9.2 Hz, 2H), 7.46 (s, 1H), 7.29 (d, J=8.4 Hz, 1H), 7.21 (t, J=8.0 Hz, 1H), 7.01 (d, 8.0 Hz, 1H) ppm. 13 C NMR (100 MHz, DMSO-d6): δ 162.1, 159.1, 158.2, 152.0, 149.7, 140.2, 139.1, 139.0, 135.0, 131.5, 129.0, 128.3, 126.3 (q), 122.3, 121.6, 121.0 (q), 120.8, 120.6, 115.8 (q), 113.0, 111.6, 108.8, 107.4 ppm. HRMS calculated for $C_{25}H_{16}ClF_6N_5O_2$ (M-H)⁻: 566.0813. Found: 566.0826.

Embodiment 21 1-(4-chloro-3-(trifluoromethyl)phenyl)-3-(3-((4-(4-(trifluoromethyl)phenyl)pyrimidin-2-yl)amino)phenyl)urea (Compound SCT-1021)

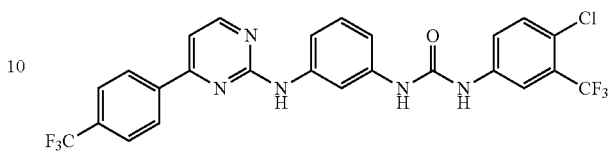

¹H NMR (400 MHz, DMSO-d6): δ 9.77 (s, 1H), 9.22 (s, 1H), 8.88 (s, 1H), 8.62 (d, J=4.8 Hz, 1H), 8.47 (d, J=8.0 Hz, 2H), 8.31 (s, 1H), 8.18 (s, 1H), 7.82 (d, J=8.0 Hz, 2H), 7.60 (s, 2H), 7.50 (d, J=4.8 Hz, 1H), 7.32 (d, J=8.0 Hz, 1H), 7.20 (t, J=8.0 Hz, 1H), 6.99 (d, J=8.0 Hz, 1H) ppm, 13 C NMR (100 MHz, DMSO-d6): δ 161.5, 159.7, 159.1, 151.9, 140.4, 140.0, 138.9 (d), 131.40, 130.2 (q), 128.2, 127.4, 126.2 (q), 125.1 (d), 124.8, 124.2 (q), 122.5, 121.7, 121.5 (q), 116.1 (q), 112.9, 111.6, 108.8, 107.9 ppm. HRMS calculated for $C_{25}H_{16}ClF_6N_5O(M-H)^-$: 550.0864. Found: 550.0874.

Embodiment 22 1-(4-chloro-3-(trifluoromethyl)phenyl)-3-(3-((6-phenyl)pyrimidin-4-yl)amino)phenyl)urea (Compound SCT-1022)

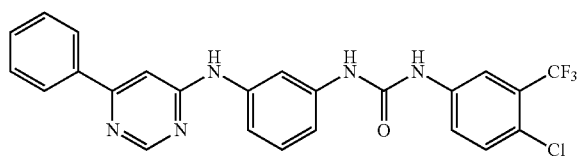

¹H NMR (400 MHz, DMSO-d6): δ 11.30 (s, 1H), 9.93 (s, 1H), 9.59 (s, 1H) 8.91 (s, 1H), 8.12 (s, 1H), 7.92 (d, J=7.2 Hz, 2H), 7.87 (s, 1H), 7.67~7.58 (m, 5H), 7.41 (d, J=8.0 Hz, 1H) 7.36 (s, 1H), 7.33 (t, J=8.0 Hz, 1H) 7.23 (d, J=8.0 Hz, 1H) ppm. 13 C NMR (100 MHz, DMSO-d6): δ 161.1, 153.4, 153.2, 152.1, 139.5, 138.9, 137.2, 131.7, 131.5, 130.5, 129.0, 128.9, 126.7, 126.1 (q), 123.7, 122.2, 121.7, 121.0 (q), 115.9 (q), 115.3, 114.8, 111.2, 102.9, 102.6 ppm. HRMS calculated for $C_{24}H_{17}ClF_3N_5O(M-H)^-$: 482.0990. Found: 482.1001.

Embodiment 23 1-(4-chloro-3-(trifluoromethyl)phenyl)-3-(3-((4-(3,5-dichlorophenyl)pyrimidin-2-yl)amino)phenyl)urea (Compound SCT-1023)

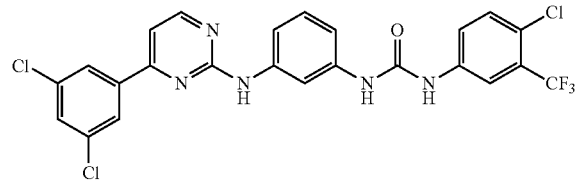

¹H NMR (400 MHz, MeOD-d4): δ 8.44 (d, J=6.4 Hz, 1H), 8.22 (d, J=2.0 Hz, 2H), 8.13 (s, 1H), 8.02 (d, J=2.8 Hz, 1H), 7.68 (t, J=2.0 Hz, 1H), 7.61 (dd, J=8.8, 2.8 Hz, 1H), 7.58 (d. J=6.4 Hz, 1H), 7.49 (d, J=8.8 Hz, 1H), 7.38 (t, J=8.0 Hz, 1H), 7.22 (d, J=8.0 Hz, 1H), 7.15 (d. J=8.0 Hz, 1H) ppm. HRMS calculated for C₂₄H₁₅Cl₃F₃N₅O(M−H)⁻: 550.0211. Found: 550.0228.

Embodiment 24 1-(3-((4-(1H-pyrrol-3-yl)pyrimidin-2-yl)amino)phenyl)-3-(3-trifluoromethyl)phenyl)urea (Compound SCT-029)

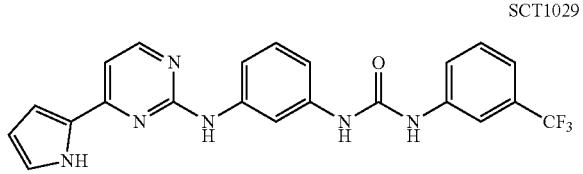 [SMILES: O=C(Nc1cccc(Nc2nccc(-c3ccc[nH]3)n2)c1)Nc1cccc(C(F)(F)F)c1]

SCT1029

¹H NMR (400 MHz, DMSO-d6): δ 11.74 (s, 1H), 10.47 (s, 1H), 9.72 (s, 1H), 9.53 (s, 1H), 8.56 (s, 1H), 8.36 (d, J=6.4 Hz, 1H), 8.02 (s, 1H), 7.60 (d, J=8.0 Hz, 1H), 7.55 (t, J=8.0 Hz, 1H), 7.38 (s, 1H), 7.34 (s, 1H) 7.32 (s, 1H), 7.28 (t, J=8.0 Hz, 1H), 7.20 (s, 1H), 7.10 (d, J=8.0 Hz, 1H), 7.00 (d, J=8.0 Hz, 1H), 6.36 (m, 1H) ppm. 13 C NMR (100 MHz, DMSO-d6): δ 159.2, 153.6, 152.5, 149.1, 140.0, 139.3, 138.0, 129.5, 128.9 (q), 128.7, 128.0, 126.3, 123.7 (q), 121.5, 117.8 (d), 116.3, 113.6 (q), 113.5 (d), 112.9, 111.3, 109.6, 104.8 ppm. HRMS calculated for C₂₂H₁₇F₃N₆O(M−H)⁻: 439.1489. Found: 439.1479.

Embodiment 25 1-(3-((4-(1H-pyrrol-3-yl)pyrimidin-2-yl)amino)phenyl)-3-(4-(trifluoromethoxy)phenyl)urea (Compound SCT-1030)

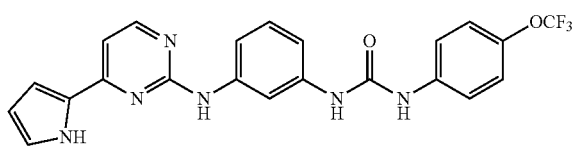

SCT1030

¹H NMR (400 MHz, DMSO-d6): δ 11.76 (s, 1H), 10.55 (s, 1H), 9.54 (s, 1H), 9.50 (s, 1H), 8.58 (s, 1H), 8.36 (d, J=6.4 Hz, 1H), 7.58 (d, J=9.2 Hz, 2H), 7.39~7.23 (m, 6H), 7.07 (d, J=8.0 Hz, 1H), 7.01 (d, J=8.0 Hz, 1H), 6.38 (m, 1H) ppm. 13 C NMR (100 MHz, DMSO-d6): δ 159.5, 153.2, 152.6, 148.3, 142.3, 139.5, 138.4, 137.8, 128.7, 128.0, 12.6,9, 121.3, 120.0 (q), 119.2, 116.8, 113.4, 112.9, 111.6, 109.7, 104.8 ppm. HRMS calculated for C₂₂H₁₇F₃N₆O₂(M+H)⁻: 455.1438. Found: 455.1429.

Embodiment 26 1-(3-((4-(1H-pyrrol-3-yl)pyrimidin-2-yl)amino)phenyl)-3-(3-chlorophenyl)urea

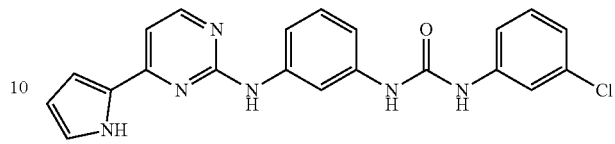

SCT1031

(Compound SCT-1031)

¹H NMR (400 MeOD-d4): δ 8.92 (s, 1H), 8.12 (d, J=6.8 Hz, 1H), 7.81 (s, 1H), 7.41 (d, J=4.0 Hz, 1H), 7.39~7.31 (m, 4H), 7.27 (d, J=8.0 Hz, 1H), 7.09 (d, J=8.0 Hz, 1H), 6.96 (d, J=8.0 Hz, 1H), 6.92 (d J=8.0 Hz, 1H), 6.48 (t, J=4.0 Hz, 1H) ppm. 13 C NMR (100 MHz, DMSO-d6): δ 159.2, 153.0, 152.2, 148.2, 140.4, 139.2, 137.7, 132.5, 129.7, 128.5, 127.8, 126.4, 120.9, 116.9, 116.5, 116.1, 113.2, 112.6, 112.3, 109.4, 104.6 ppm. HRMS calculated for C₂₁H₁₇ClN₆O(M+H)⁻: 405.1225. Found: 405.1217.

Embodiment 27 1-(3-((4-(1H-pyrrol-3-yl)pyrimidin-2-yl)amino)phenyl)-3-(3,5-dichlorophenyl)Urea (Compound SCT-1032)

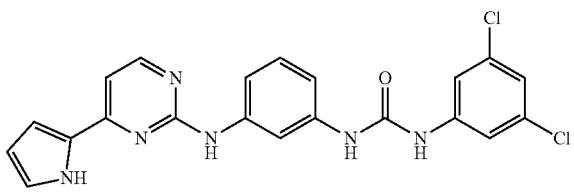

SCT1032

¹H NMR (400 MHz, DMSO-d6): δ 11.67 (s, 1H), 10.3 (s, 1H), 977 (s, 1H), 9.50 (s, 1H), 8.62 (s, 1H), 8.34 (d, J=6.4 Hz, 1H), 7.56 (d, J=6.4 Hz, 2H), 7.36 (s, 1H), 7.30 (d, J=6.4 Hz, 1H), 7.26 (s, 1H), 7.25 (d, J=8.0 Hz, 1H), 7.17 (s, 1H), 7.07 (d, J=8.0 Hz, 1H), 6.94 (d, J=8.0 Hz, 1H), 6.38 (s, 1H) ppm. 13 CNMR (100 MHz, DMSO-d6): δ 159.0, 154.1, 152.2, 149.7, 141.7, 139.0, 138.2, 133.7, 128.7, 128.1, 125.9, 120.6, 115.9, 115.8, 113.6, 112.8, 111.2, 109.6, 104.8 ppm. HRMS calculated for C₂₁H₁₆Cl₂N₆O(M+H)⁻: 439.0835. Found: 439.0827.

Embodiment 28

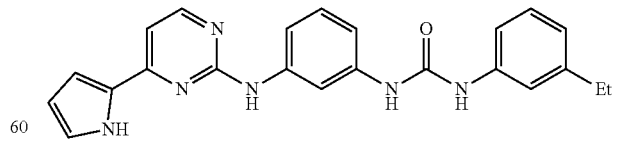

SCT1033

1-(3-(4-(1H-pyrrol-3-yl)pyrimidin-2-yl)amino)phenyl)-3-(3-ethylphenyl)urea (Compound SCT-1033)

¹H NMR (400 MHz, DMSO-d6): δ 11.82 (s, 1H), 10.54 (s, 1H), 9.45 (s, 1H), 9.24 (s, 1H), 8.70 (s, 1H), 8.36 (d, J=6.4

Hz, 1H), 7.40 (s, 1H), 7.38~7.20 (m, 6H), 7.04 (d, J=8.0 Hz, 1H), 6.94 (d, J=8.0 Hz, 1H), 6.86 (d, J=7.6 Hz, 1H) 6.39~6.37 (m, 1H), 2.58 (q, J=7.6 Hz, 2H), 1.17 (t, J=7.6 Hz, 3H) ppm. 13 C NMR (100 MHz, DMSO-d6): δ 159.3, 153.4, 152.6, 148.7, 143.9, 139.7, 139.0, 137.9, 128.6, 128.2, 128.0, 126.5, 121.1, 117.4, 116.5, 115.5, 113.0, 112.6, 111.4, 109.4, 104.7, 27.8, 15.1 ppm. HRMS calculated for $C_{23}H_{22}N_6O(M+H)^-$: 399.1928. Found: 399.1919.

Embodiment 29 1-(3-((4-((1H-pyrrol-3-yl)pyrimidin-2-yl)amino)phenyl)-3-(2-fluoro-5-methylphenyl)urea (Compound SCT-1034)

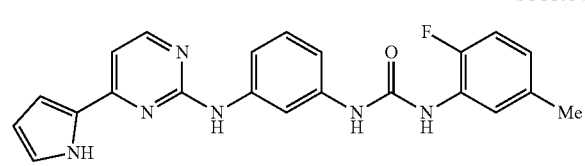

SCT1034

$^1$H NMR (400 MHz, DMSO) δ 11.74 (s, 1H), 10.35 (s, 1H), 9.57 (s, 1H), 8.75 (s, 1H), 8.71 (s, 1H), 8.37 (d, J=5.6 Hz, 1H), 7.94 (d, J=7.6 Hz, 1H), 7.31~7.24 (m, 3H), 7.15~7.07 (m, 3H), 6.91 (d, J=7.6 Hz, 1H), 6.8:5 (s, 1H), 6.36 (s, 1H), 2.29 (s, 3H) ppm. 13 C NMR (100 MHz, DMSO-d6): δ 158.7, 154.5, 152.1, 151.4, 150.4, 149.0, 139.3, 138.5, 132.8 (d), 128.5, 128.1, 126.2 (d), 125.4, 122.7 (d), 121.1, 115.3, 114.2 (d), 113.0, 112.1, 111.0, 109.1, 104.8, 20.1 ppm. HRMS calculated for $C_{22}H_{19}FN_6O(M+H)^-$: 403.1677. Found: 403.1669.

Embodiment 30 1-(3-((4-(1H-pyrrol-3-yl)pyrimidin-2-yl)amino)phenyl)-3-(3,5-bis(trifluoromethyl)phenyl)urea (Compound SCT-1035)

SCT1035

$^1$H NMR (400 MHz, DMSO-d6): δ 11.75 (s, 1H), 10.57 (s, 1H), 10.26 (s, 1H), 9.72 (s, 1H), 8.46 (s, 1H), 8.37 (d, J=6.4 Hz, 1H), 8.12 (s, 2H), 7.64 (s, 1H), 7.42 (s, 1H), 7.35 (d, J=6.4 Hz, 1H), 7.31 (t, J=8.0 Hz, 1H), 7.23 (s, 1H), 7.15 (d, J=8.0 Hz, 1H), 7.06 (d, J=8.0 Hz, 1H), 6.37~6.35 (m, 1H) ppm 13 C NMR (100 MHz, DMSO-d6): δ 159.5, 153.0, 152.2, 148.2, 141.3, 139.0, 137.7, 130.3 (q), 128.8, 127.9, 126.8, 122.8 (q), 117.2, 116.8, 114.0, 113.9, 113.3, 111.3, 109.9, 104.7 ppm.

Embodiment 31 1-(4-((4-(1H-pyrrol-2-yl)pyrimidin-2-yl)amino)phenyl)-3-(4-chloro-3-(trifluoromethyl)phenyl)urea (Compound SCT1036)

SCT1036

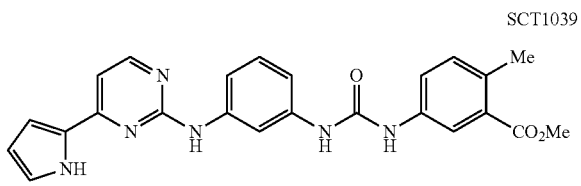 [SMILES: COC(=O)c1cc(NC(=O)Nc2cccc(Nc3nccc(-c4ccc[nH]4)n3)c2)ccc1C]

$^1$H NMR (400 MHz, DMSO-d6): δ 11.42 (s, 1H), 9.27 (s, 1H), 9.08 (s, 1H), 8.66 (s, 1H), 8.32 (d, J=5.2 Hz, 1H), 8.11 (s, 1H), 7.74 (d, J=8.8 Hz, 2H), 7.64~7.58 (m, 2H), 7.37 (d, J=8.8 Hz, 2H), 7.06~7.04 (m, 2H), 6.95 (s, 1H), 6.22 (s, 1H) ppm. HRMS calculated for $C_{22}H_{16}ClF_3N_6O(M+H)^-$: 473.1099. Found: 473.1092.

Embodiment 32 Methyl 3-(3-(4-(1H-pyrrol-3-yl)pyrimidin-2-yl)amino)phenyl)ureido)benzoate (Compound SCT-1037)

SCT1037

$^1$H NMR (400 MHz, DMSO-d6): δ 11.72 (s, 1H), 10.49 (s, 1H), 9.60 (s, 1H), 9.51 (s, 1H), 8.65 is 1H), 8.35 (d, J=6.4 Hz, 1H), 8.24 (s, 1H), 7.63 (d, J=8.0 Hz, 1H), 7.59 (d, J=7.6 Hz, 1H), 7.47 (t, J=7.6 Hz, 1H), 7.38 (s, 1H), 7.33 (d, J=6.4 Hz, 1H), 7.30 (s, 1H), 7.27 (d, J=8.0 Hz, 1H), 7.06 (d, J=8.0 Hz, 1H), 6.96 (d, J=8.0 Hz, 1H), 6.40~6.38 (m, 1H), 3.84 (s, 3H) ppm. 13 C NMR (100 MHz, DMSO-d6): δ 165.7, 159.2, 153.6, 152.5, 149.0, 140.0, 139.4, 138.0, 130.0, 128.8, 128.7, 127.9, 126.6, 122.4, 122.3, 118.0, 116.4, 113.3, 112.7, 111.4, 109.5, 104.8, 51.7 ppm. HRMS calculated for $C_{23}H_{20}N_6O_3(M+H)^-$: 429.1670. Found: 429.1663.

Embodiment 33 Methyl 5-(3-(3-((4-(1H-pyrrol-2-yl)pyrimidin-2-yl)amino)phenyl)ureido)-2-methylbenzoate (Compound SCT-1039)

SCT1039

$^1$H NMR (400 MHz, DMSO-d6): δ 11.67 (s, 1H), 10.25 (s, 1H), 9.32 (s, 1H), 9.30 (s, 1H), 8.70 (s, 1H), 8.34 (d, J=5.6 Hz, 1H), 8.06 (s, 1H), 7.49 (d, J=8.4 Hz, 1H), 7.29~7.23 (m, 4H), 7.19 (s, 1H) 7.04 (d, J=8.0 Hz, 1H), 6.90 (d, J=8.0 Hz, 1H), 6.36 (s, 1H), 3.81 (s, 3H), 2.45 (s, 3H) ppm. 13 C NMR (100 MHz, DMSO-d6): δ 166.8, 158.7, 154.6, 152.5, 150.6, 139.4, 138.5, 137.0, 131.9, 131.5, 129.1, 128.5, 128.1, 125.6, 121.6, 119.1, 115.3, 113.0, 112.3, 111.1, 109.3, 104.8, 51.4, 19.9 ppm. HRMS calculated for $C_{24}H_{22}N_6O_3(M+H)^-$: 443.1826. Found: 443.1822.

Embodiment 34 Methyl 5-(3-(3-((4-(1H-pyrrol-2-yl)pyrimidin-2-yl)amino)phenyl)ureido)-2-chlorobenzoate (Compound SCT-1041)

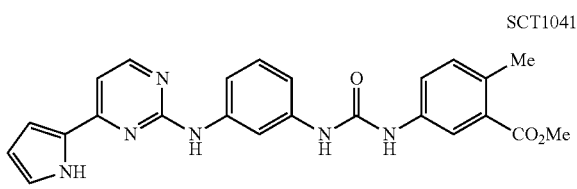 [SMILES: COC(=O)c1cc(NC(=O)Nc2cccc(Nc3nccc(-c4ccc[nH]4)n3)c2)ccc1C]

SCT1041

$^1$H NMR (400 MHz, MeOD-d4): δ 8.95 (s, 1H), 8.33 (s, 1H), 8.15 (d, J=6.8 Hz, 1H), 7.75 (d, J=7.6 Hz, 1H), 7.64 (d, J=8.4 Hz, 1H), 7.50 (t, J=7.6 Hz, 1H), 7.44~7.41 (m, 2H), 7.38 (t, J=8.0 Hz, 1H), 7.34 (d, J=7.6 Hz, 1H), 6.98~6.92 (m, 2H), 6.49~6.47 (m, 1H), 3.93 (s, 3H) ppm. 13 C NMR (100 MHz, DMSO-d6): δ 165.7, 159.2, 153.5, 151.5, 149.0, 139.5, 139.4, 138.0, 129.7, 128.8, 128.7, 127.9, 126.6, 122.4, 122.3, 118.0, 116.4, 113.3, 112.7, 111.4, 109.5, 104.8, 51.7 ppm. HRMS calculated for $C_{23}H_{19}ClN_6O_3(M+H)^-$: 463.1280. Found: 463.1280.

Embodiment 35 3-(3-(3-((4-(1H-pyrrol-2-yl)pyrimidin-2-yl)amino)phenyl)ureido)benzoic acid (Compound SCT-11038)

SCT1038

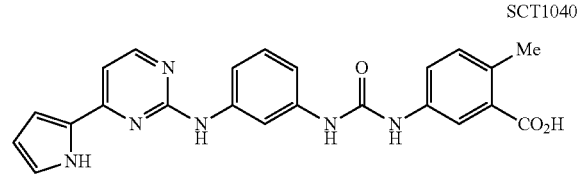 [SMILES: Cc1ccc(NC(=O)Nc2cccc(Nc3nccc(-c4ccc[nH]4)n3)c2)cc1C(=O)O]

$^1$H NMR (400 MHz, DMSO-d6): δ 11.36 (s, 1H), 9.44 (s 1H), 9.03 (s, 1H), 8.85 (s, 2H), 8.33 (d, J=5.2 Hz, 1H), 8.19 (s, 1H), 7.63~7.59 (m, 2H), 7.44 (t, J=8.0 Hz, 1H), 7.16 (t, J=8.0 Hz, 1H), 7.10~7.06 (m, 3H), 7.02 (s, 1H), 6.76 (d, J=8.0 Hz, 1H), 6.22~6.21 (m, 1H) ppm. HRMS calculated for $C_{22}H_{18}N_6O_3(M+H)^-$: 415.1513. Found: 415.1507.

Embodiment 36 5-(3-(3-((4-(1H-pyrrol-3-yl)pyrimidin-2-yl)amino)phenyl)ureido)-2-methylbenzoic acid (Compound SCT-1040)

SCT1040

$^1$H NMR (400 MHz, DMSO-d6): δ 12.89 (s, 1H), 11.39 (s, 1H), 9.48 (s, 1H), 8.86 (s, 2H), 8.76 (s, 1H), 8.33 (d, J=5.2 Hz, 1H), 8.01 (s, 1H), 7.51 (dd, J=8.4, 2.4 Hz, 1H), 7.25 (d, J=8.4 Hz 1H), 7.16 (t, J=8.0 Hz, 1H), 7.10~7.02 (m, 4H), 6.74 (d, J=8.0 Hz, 1H), 6.24~6.22 (m, 1H), 2.47 (s 3H) ppm. 13 C NMR (100 MHz, DMSO-d6): δ 168.2, 159.3, 157.4, 156.3, 152.4, 140.8, 139.1, 136.8, 131.9, 131.4, 130.3, 128.8, 128.1, 122.2, 121.4, 119.6, 112.1, 111.0, 110.4, 109.7, 108.0, 105.1, 20.1 ppm.

Embodiment 37

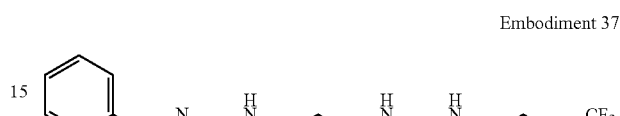

Embodiment 38

Embodiment 39

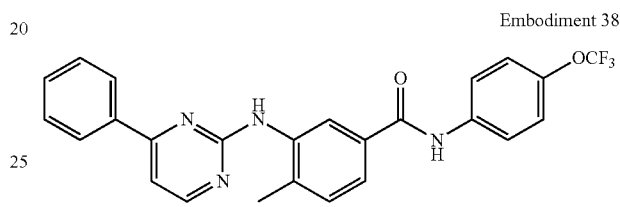

Embodiment 40

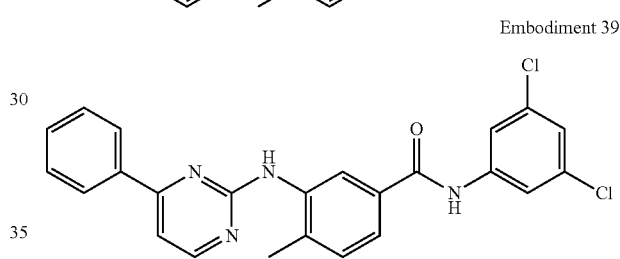

Embodiment 41

Embodiment 42

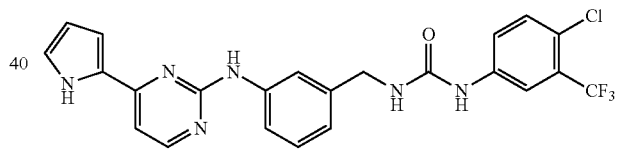

Embodiment 43

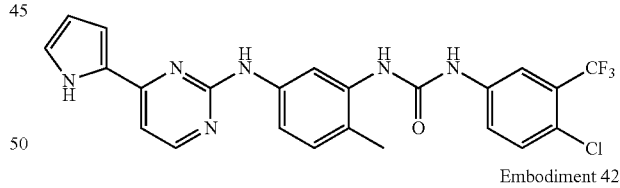

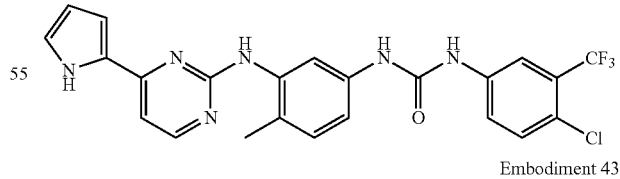

Embodiment 44
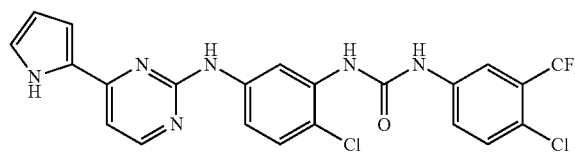
Embodiment 45
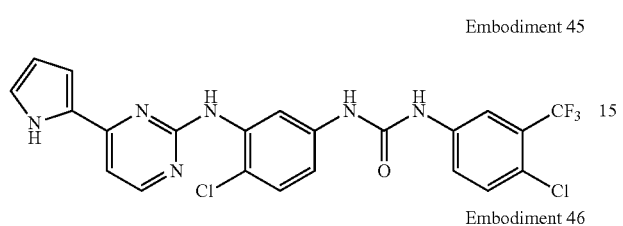
Embodiment 46
Embodiment 47
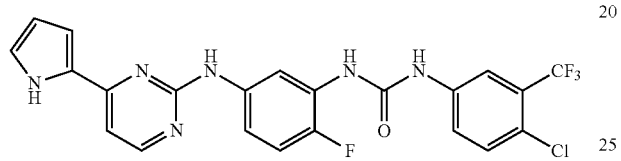
Embodiment 48
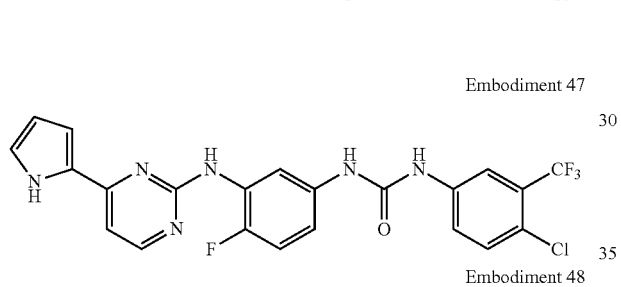
Embodiment 49
Embodiment 50
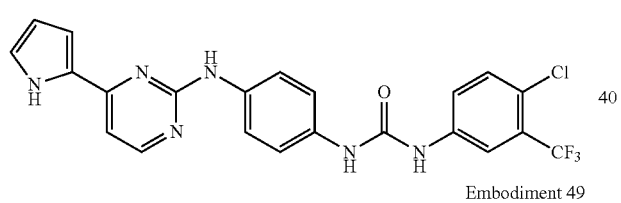
Embodiment 51
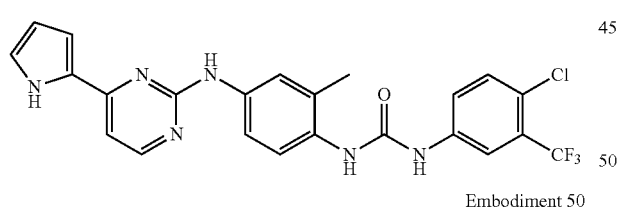
Embodiment 52
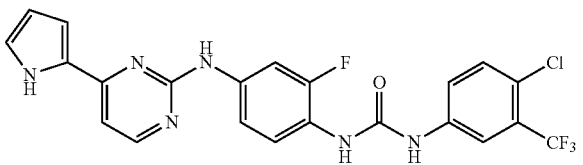
Embodiment 53
Embodiment 54
Embodiment 55
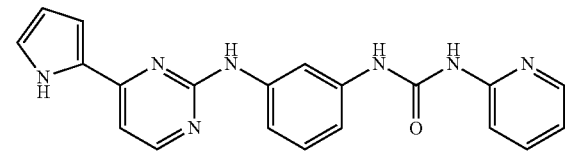
Embodiment 56
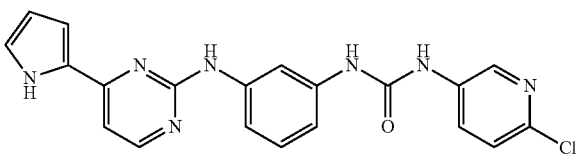
Embodiment 57
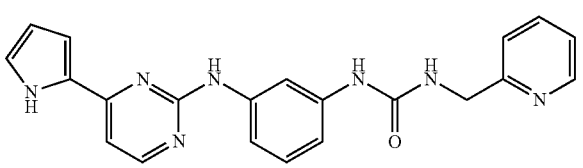
Embodiment 58
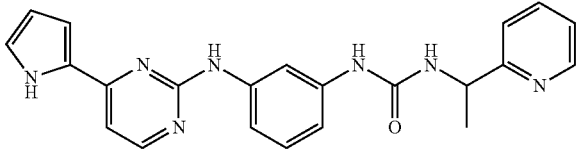
Embodiment 59
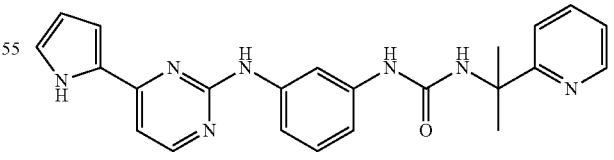

Biological Activity Assay

In order to investigate the pharmacological properties of the compounds of the present invention, the effects on the AMPK activity, the survival rate of cancer cells, and the growth of adipocytes are studied respectively.

Cell Line

Hepatoma cell Huh-7 was obtained from Health Science Research Resources Bank (HSRRB, Osaka. Japan; JCRB0403); Hepatoma cell PLC/PRF/5 (PLC5), Sk-Hep-1 and HCC1806 were obtained from the American Type Culture Collection (ATCC, Manassas, Va.). All cell lines are cultured immediately and frozen, so the frozen cells can be thawed every 3 months to allow experiments are conducted with the same batch of cells.

AMPK Enzyme Activity Assay

The protein extract of liver cancer cell PLC5 and the anti-AMPKα1 antibody were incubated in an immunoprecipitation buffer (G-Biosciences) overnight. Protein A/G Magnetic Beads (PureProteome™) are added to each sample respectively and incubated at 4° C. for 4 hours. In the case of the recombinant protein AMPK, 12.5 ng of the recombinant protein human AMPK (α1, β1, γ1) is incubated with various doses of the compound, and then AMPK activities are detected based on the manual of the SAMS peptide assay (Cyclex).

Figure 1B:
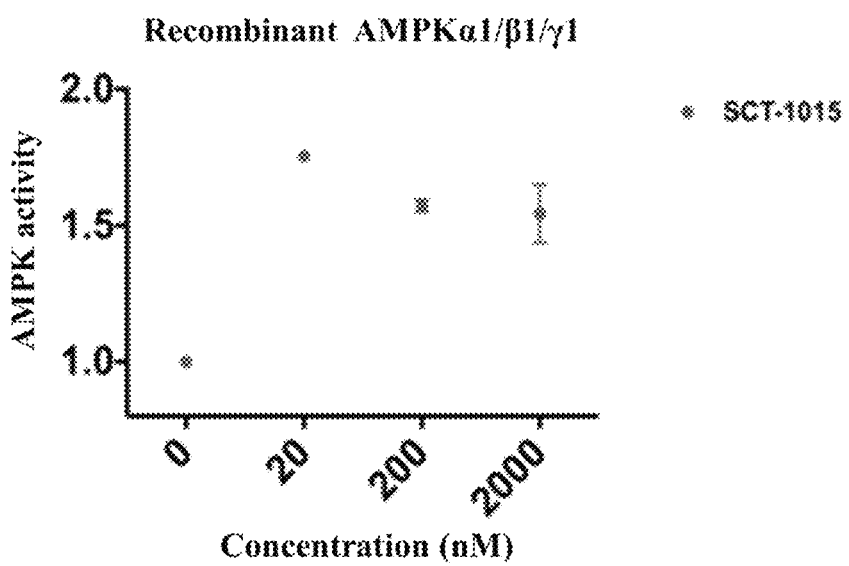

As shown in FIG. 1A, AMPK activity was examined after addition of 20-20,000 nM of compound SCT-1015 to AMPKα1 immunoprecipitated protein extract, and AMPK, activity shows significant increase compared to the group without compound addition. As shown in FIG. 1B, the recombinant protein AMPKα1/β1/γ1 is incubated with the compound SCT-1015 of 20-2,000 nM, and the activity of the recombinant protein AMPKα1/β1/γ1 also shows significant increase compared with the group without compound addition. It is shown by FIGS. 1A and 1B that the SCT-1015 compound can increase the activity of AMPK in liver cancer cells.

Detection of AMPK Phosphorylation by ELISA Assay

In this analysis, the commercial kit AMPK [pT17] Phospho-ELISA Kit (KHO0651) produced by ThermoFisher Science is utilized. The hepatoma cell PLC5 is cultured with 10 µM of the compound for 24 hours, and the analysis is performed according to the manual, and the absorbance was detected at a wavelength of 450 nm.

As shown in Table 3, the derivatives are able to induce AMPK phosphorylation at the position of T172, and the compound SCT-1015 is most effective (1.8 fold compared to control group).

TABLE 3

AMPK phosphorylation

| SCT CPD | IC$_{50}$(PLC5, 48 hr) | AMPK T172 activity |
|---|---|---|
| 1 | >20 | |
| 2 | >20 | 1.2 |
| 3 | >20 | 1.1 |
| 4 | >20 | 1.1 |
| 5 | >20 | 1.0 |
| 6 | >20 | 1.3 |
| 7 | >20 | 1.1 |
| 8 | >20 | 1.0 |
| 9 | >20 | 1.1 |
| 10 | >20 | 1.0 |
| 11 | >20 | 1.1 |
| 12 | >20 | 1.0 |
| 13 | >20 | 1.0 |
| 14 | >20 | 1.0 |
| 15 | 12.1 | 1.8 |
| 16 | >20 | 1.0 |
| 17 | >20 | 1.1 |
| 18 | >20 | 1.1 |
| 19 | >20 | 1.0 |
| 20 | >20 | 1.3 |
| 21 | >20 | 1.2 |
| 22 | >20 | 1.4 |
| 23 | >20 | |
| 29 | | |
| 30 | 13.7 | |
| 31 | >20 | |
| 32 | 17.3 | |
| 33 | >20 | |
| 34 | >20 | |
| 35 | >20 | |
| 36 | 15.2 | |
| 37 | >20 | |
| 38 | >20 | |
| 39 | >20 | |
| 40 | >20 | |
| 41 | >20 | |

Detection of AMPK Phosphorylation by Immuno-Blot Assay

Figure 2A:
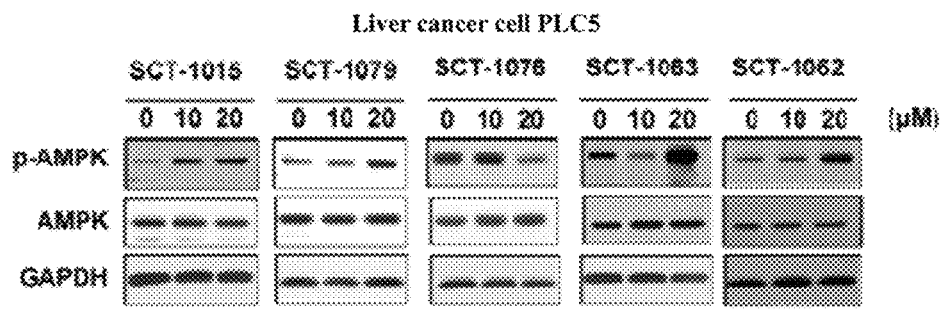
FIG. 2A-2C depict the compounds of the invention phosphorylate AMPK
Figure 2B:
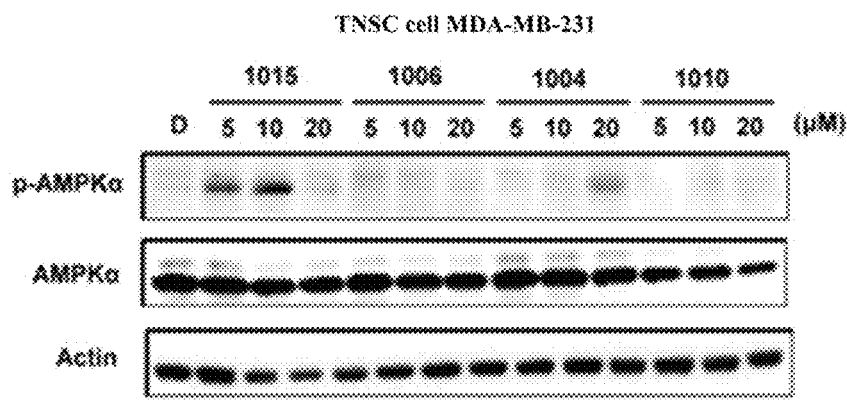
Figure 2C:
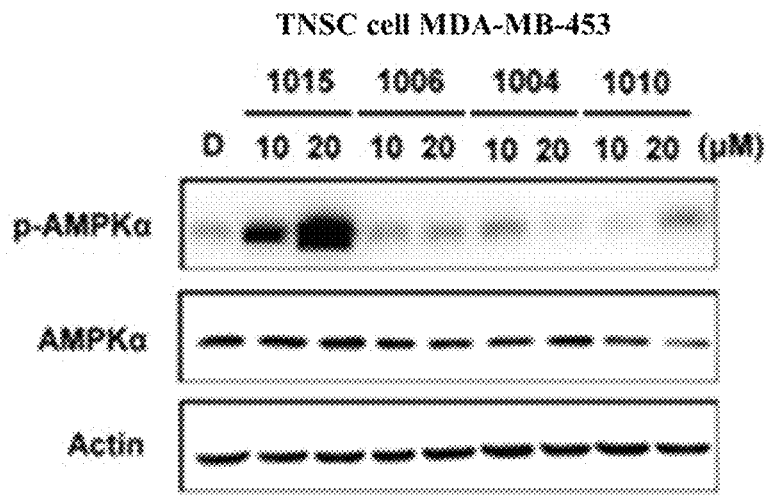
Figure 2D:
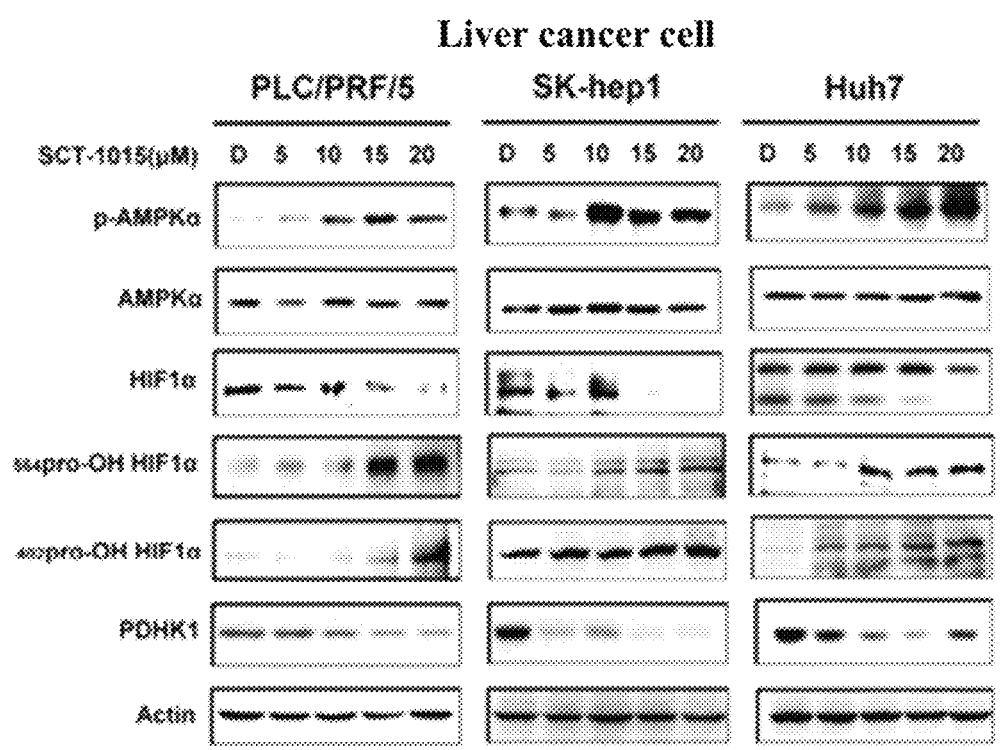
FIG. 2D depicts the compound SCT-1015 phosphorylates AMPK and further regulates downstream signaling molecules.

The liver cancer cell PCL5 and the triple negative breast cancer cell (TNBC) MBA-MB-231 and MDA-MB-453 are cultured with the compound SCT-1015, respectively. The cells are collected, wash, and lysed by RIPA buffer to obtain a protein extract. The protein concentration was measured by Bio-Rad Protein Assay dye reagent (Bio-Rad). The protein samples are diluted with 2 times SDS-loading buffer (100 mM Tris HCl, pH 6.8, 200 mM β-mercaptoethanol, 4% SDS, 0.02% bromophenol blue, and 20% glycerol) to adjust volume, and electrophoresis is carried out using 10% SDS polyacrylamide gels and followed by transferring to PVDF membrane. The primary antibody is added to detect the target protein on the membrane, and then the secondary antibody with horseradish peroxidase is added, followed by addition of substrate (enhanced SuperSignal West Pico Cheminlumiescent Substrate, Pierce) to obtain the signal of the specific protein. and the protein content is determined by β-actin. The β-actin is used as an internal control for protein amount. As shown in FIGS. 2A to 2C, the group of treating compound SCT-1015, compared with the non-treated group, the expression of phosphorylated AMPKα (p-AMPKα) was significantly increased. As shown in FIG. 2D, the phosphorylated AMPK further regulates the downstream signaling molecules HIF1 and PDHK1 in PLC/PRF/5, SK-hep1, and Huh-7; from the above results, it can be seen that the compound SCI-1015 of the present invention can phosphorylate and activate AMPKα, and further regulate downstream information in the three liver cancer cell lines PLC/PRF/5. SK-hep1 and Huh-7, the phosphorylation-activated AMPK system further regulates the downstream signaling molecules HIF1 and PDHK1. The results demonstrate that the compound SCT-1015 activates AMPKα and further regulate the downstream signaling pathway, thereby affecting the related biochemical reactions in the cells.

Cell Viability of Liver Cancer Cells (Cytotoxicity Effect)

Figure 3:
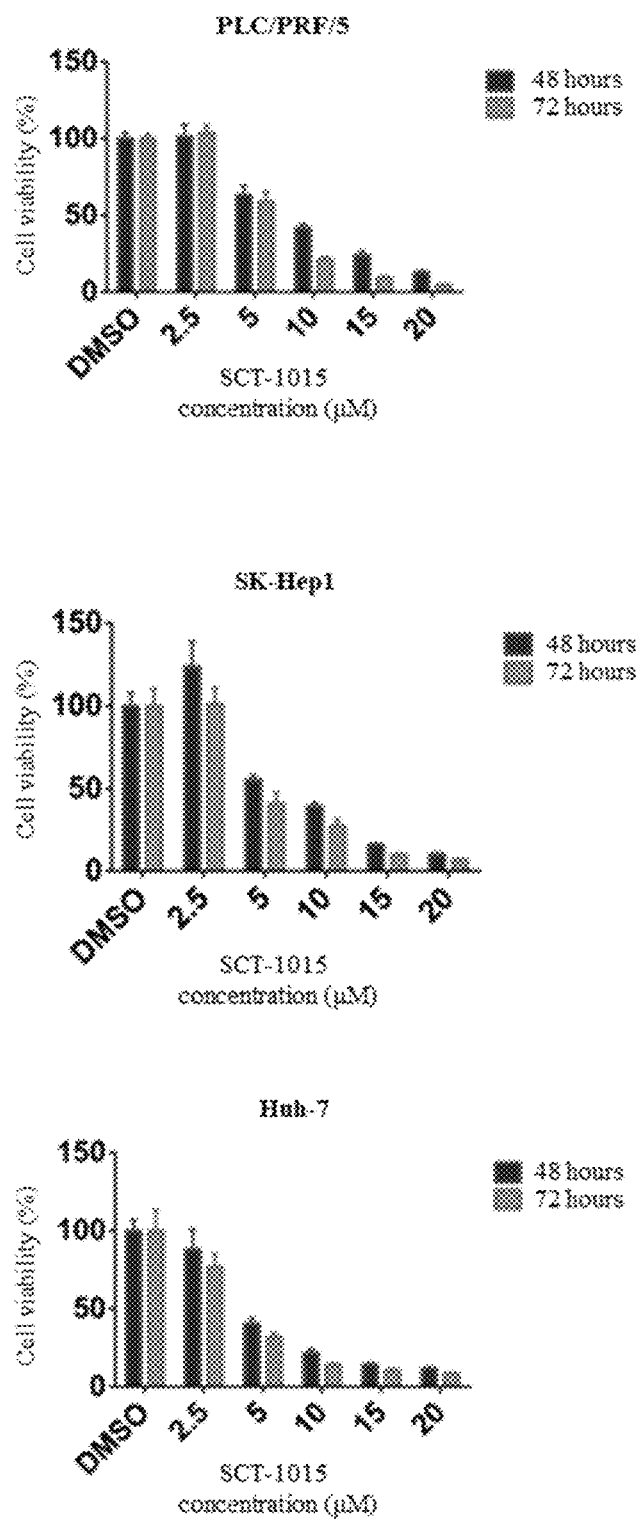
FIG. 3 depicts the compound SCT-1015 inhibits the growth of hepatic cancer cells.

Analysis is performed using a commercial kit Prestoblue assay produced by Thermo Fisher Scientific. Three liver cancer cell lines PLC/PRF/5, SK-hep1, and Huh-7 are cultured with compound SCT-1015 for 48 hours and 72 hours, respectively. As shown in FIG. 3, the addition of 5-20 µM of the compound SCT-1015 to the liver cancer cell line, inhibit the cell proliferation significantly compared with the control group (DMSO). The results support that the compound of the present invention can activate AMPK to inhibit the proliferation of liver cancer cells.

Cell Viability of Triple Negative Breast Cancer Cells

An in situ triple negative breast cancer mouse model (HCC1806/luc2-bearing orthotopic mice) is established with HCC1806 cells carrying the luciferase (luc2) gene. The experimental mice are divided into two groups, namely (1) control group: solvent; (2) experimental group: compound SCT-1015 (20 mg/kg), and the mice are fed daily for 14 days. On day 0 and day 14, the substrate of luciferase is injected into the peritoneal cavity of mice, and the luminescence from HCC1806/luc2 cells is detected by in vivo imaging system (IVIS) to monitor cell growth.

Figure 4:
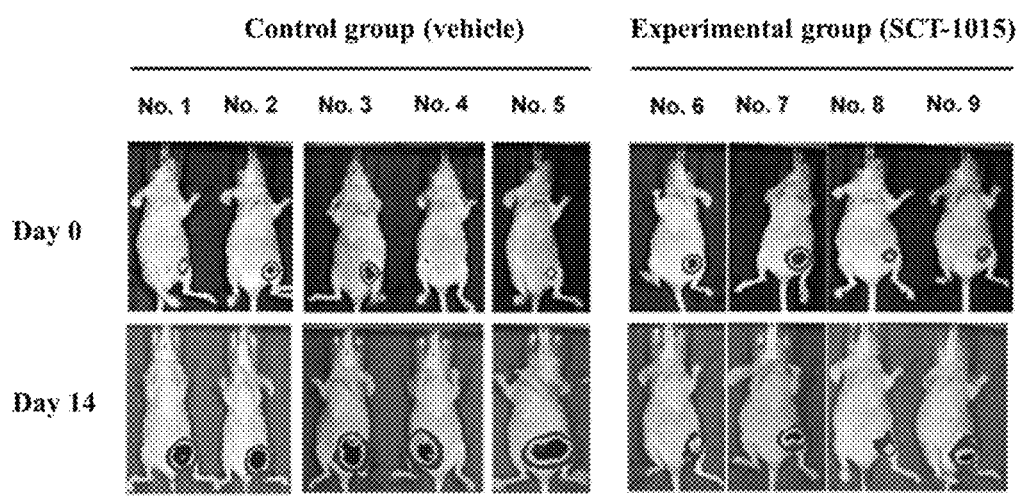
FIG. 4 depicts the compound SCT-0015 inhibits the growth of triple-negative breast cancer cells.

As shown in FIG. 4, On day 14, the number of HCC1806/luc2 cell of the mice fed the compound SCT-1015 does not show noteworthy increase compared to day 0, but significantly less than the number of the control group on day 14. The results support that the compound of the present invention can activate AMPK to inhibit the growth of triple-negative breast cancer cells.

Cell Growth of Adipocytes

According to the standard procedure of adipocyte differentiation, human pre-adipocytes are treated with adipogenesis reagent (Gibco StemPro) for 14 days to induce differentiation into mature adipocytes. Next, mature adipocytes are treated with different concentrations of compound SCT-1015 (100 µM, 25 µM, 12.5 µM, 5 µM, and 2.5 µM), solvent only (Mock), or non-treated and cultivated for 48 hours. Then, the adipocytes are stained with adipoRed (Lonza inc.), and the cell number is evaluated by fluorescence signals measured at excited and emission wavelength are 485 nm and 572 nm, respectively. In addition, after the cells were treated with 2.5 µM. of the compound SCT-1015, the cell morphology was also observed through cell imaging.

Figure 5A:
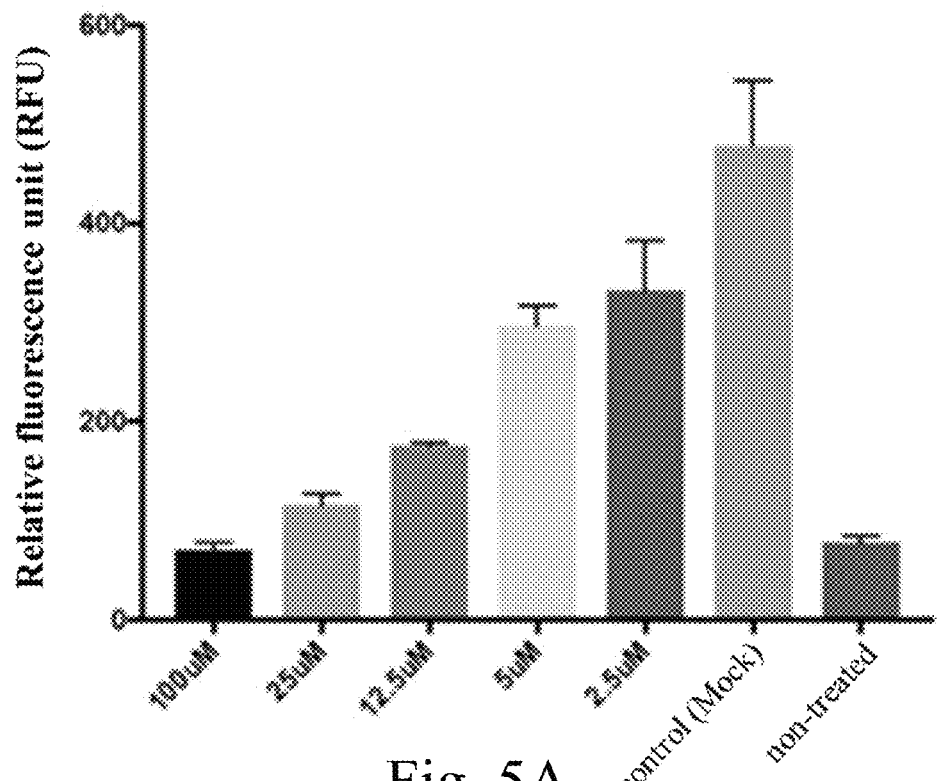
FIGS. 5A and 5B depict the compound SCT-0015 induces apoptosis of adipocytes.
Figure 5B:
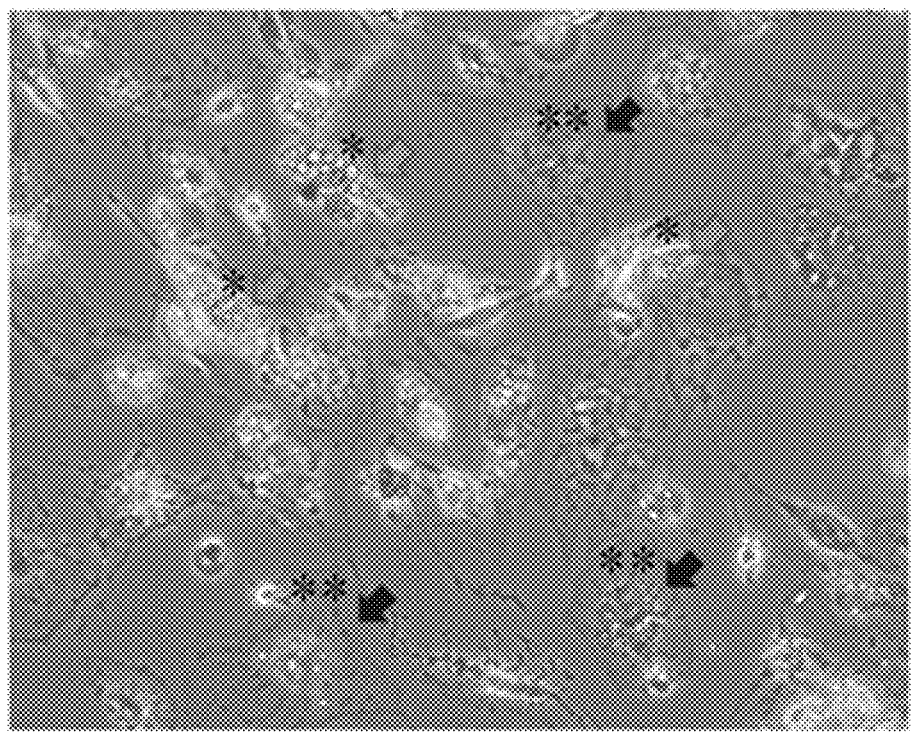

As shown in FIG. 5A, comparing to the control group (Mock), the number of the mature adipocytes is significantly decreased after treatment of the compound SCT-1015, and shows dose-dependent manner. As shown in FIG. 5B, the mature adipocytes (marked ) under the treatment of 2.5 µM of the compound SCT-1015 shows a pattern of shrinkage and death. However, the undifferentiated cells (marked )

still maintain a healthy cell morphology. The above experimental results demonstrate that the compound of the present invention is capable of inducing apoptosis of adipocytes and is not toxic to undifferentiated cells.

Figure 6:
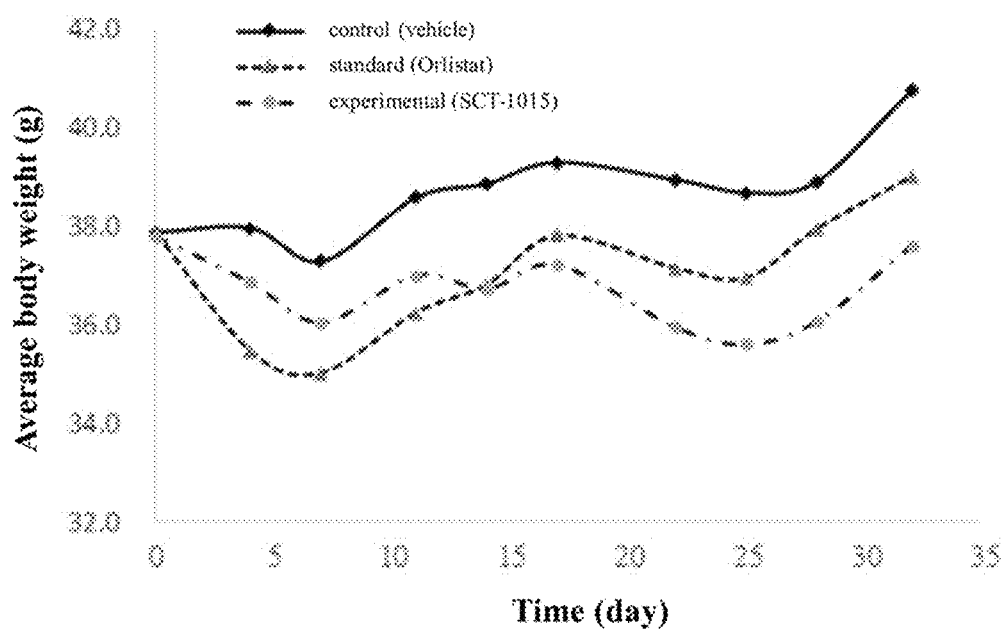
FIG. 6 depicts feeding obese mouse the compound SCT-0015 reduces their body weight.

Treatment of Diet-Induced Obesity (DIO) Mice with the Compounds of the Invention The male mice C57BL/6 were purchased from the National Laboratory Animal Center (NLAC, Taipei, Taiwan) and fed high-fat-die for 4 weeks to establish the diet-induced obesity (DIO) mouse model for subsequent experiments As shown in FIG. 6, comparing to the control group of mice, mice treated with compound SCT-1015 lost an average of 5% of their body weight, and are similar to the mice treated with standard orlistat. It shows that the compound of the present invention can reduce the body weight of the DIO mice by affecting the activity of AMPK and thereby inducing apoptosis of the adipocytes.

In summary, the compounds disclosed in the present invention possess a novel chemical structure and act as an agonist of adenosine monophosphate-activated protein kinase. The compound of the present invention can bind to AMPK α subunit to induce phosphorylation and activation of AMPKα, thereby further regulating downstream signaling molecules, inhibiting growth and proliferation of liver cancer cells and breast cancer cells, and also inducing apoptosis of adipocytes. Therefore, the compound provided by the present invention can be utilized for preparing a pharmaceutical composition for cancer, and lipid metabolism-related diseases or syndromes mediated by AMPK. The compound provided by the present invention can be applied to the treatment of cancer, and lipid metabolic disorder mediated by AMPK. Accordingly, the present invention provides a novel compound with medical potential which has improved AMPK activation efficacy and therapeutic specificity compared to the prior art.

The invention claimed is:

1. A compound of the formula (I):

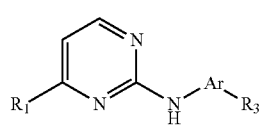

(I)

or a pharmaceutically acceptable salt thereof, wherein $R_1$ is an unsubstituted or substituted aromatic group; $R_3$ is selected from the group consisting of a phenyl urea group substituted by —$CF_3$, —Cl, —$OCF_3$, —$CH_3$, —$C_2H_5$, —COOMe, —COOH, or a combination thereof and a substituted

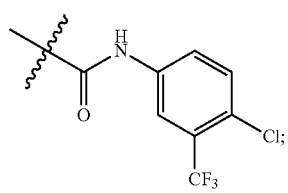 [SMILES: *C(=O)Nc1ccc(Cl)c(C(F)(F)F)c1]

Ar is an unsubstituted or substituted phenylene group.

2. The compound, or a pharmaceutically acceptable salt thereof according to claim 1, wherein the unsubstituted or substituted phenylene group is

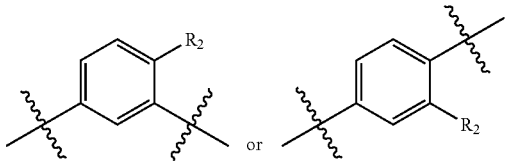

and $R_2$ is a hydrogen atom, a halide, or an alkyl group.

3. The compound, or a pharmaceutically acceptable salt thereof according to claim 1, wherein $R_1$ is an unsubstituted aromatic group, a substituted aromatic group, a substituted

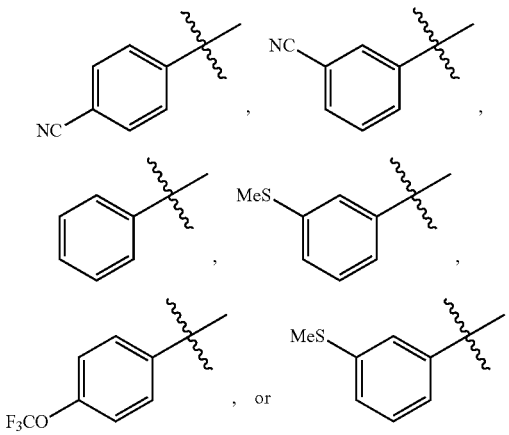

4. The compound, or a pharmaceutically acceptable salt thereof according to claim 1, wherein $R_1$ is an unsubstituted pyrrolic group, a substituted pyrrolic group, or a substituted

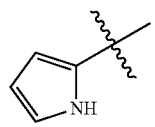

5. The compound, or a pharmaceutically acceptable salt thereof according to claim 1, wherein $R_1$ is an unsubstituted thiophene group, a substituted thiophene group, or a substituted

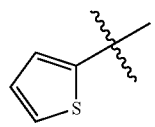

6. The compound, or a pharmaceutically acceptable salt thereof according to claim 1, wherein $R_1$ is an unsubstituted naphthalenic group, a substituted naphthalenic group, or a substituted

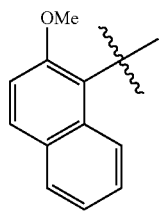

7. The compound, or a pharmaceutically acceptable salt thereof according to claim 1, wherein $R_1$ is a di-substituted phenyl group, a substituted

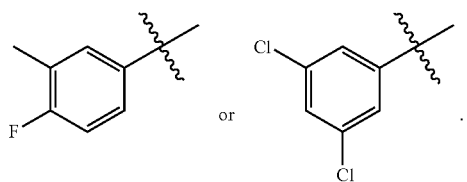

8. The compound, or a pharmaceutically acceptable salt thereof according to claim 1, wherein the substituted phenyl urea group of $R_3$ is a substituted

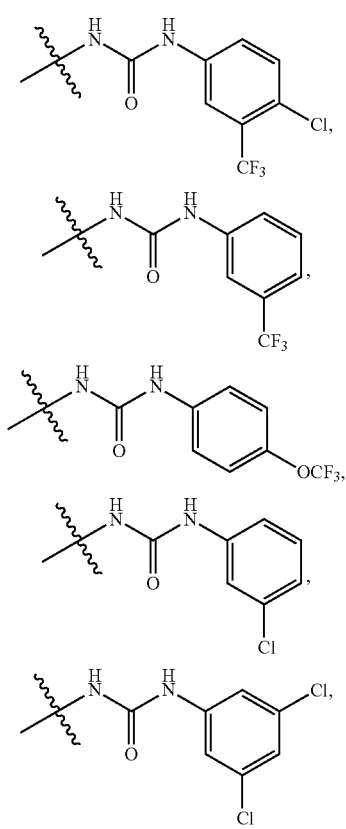

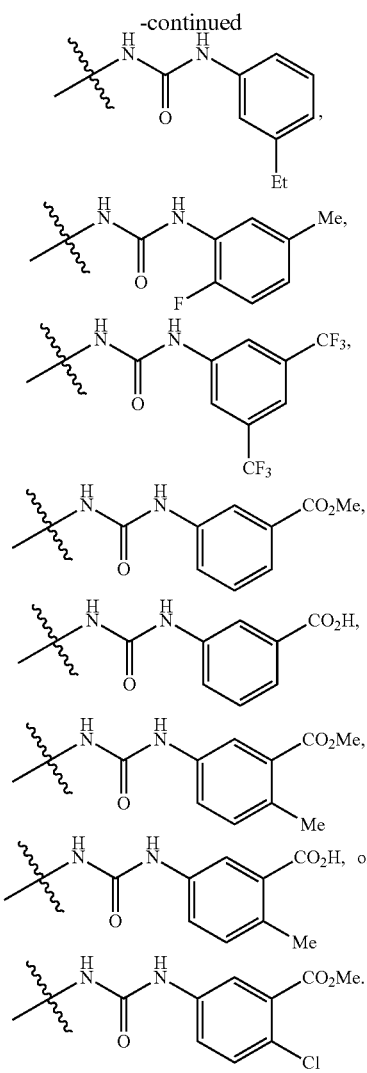

9. The compound, or a pharmaceutically acceptable salt thereof according to claim 2, wherein the halide of $R_2$ is a fluoride or a chloride.

10. The compound, or a pharmaceutically acceptable salt thereof according to claim 2, wherein the alkyl group of $R_2$ is a methyl group or an ethyl group.

11. A method of treating a cancer associated with adenosine monophosphate-activated protein kinase, and lipid metabolic disorder or lipid metabolic syndrome, which comprises administering an effective amount of the compound of claim 1, or a pharmaceutically acceptable salt thereof.

12. The method according to claim 11, wherein the cancer is liver cancer or breast cancer.

13. The method according to claim 11, wherein the compound has binding specificity for the alpha subunit of adenosine monophosphate-activated protein kinase and induce phosphorylation of the alpha subunit of adenosine monophosphate-activated protein kinase.

14. The method according to claim 11, wherein the compound induces apoptosis of adipocytes.

* * * * *